United States Patent
Kitabata et al.

(10) Patent No.: US 11,931,290 B2
(45) Date of Patent: Mar. 19, 2024

(54) WATER ABSORBENT RESIN POWDER FOR HEAT-GENERATING ELEMENT COMPOSITION, AND HEAT-GENERATING ELEMENT COMPOSITION

(71) Applicant: NIPPON SHOKUBAI CO., LTD., Osaka (JP)

(72) Inventors: Sachie Kitabata, Himeji (JP); Shigeru Sakamoto, Himeji (JP); Sumito Kumagai, Himeji (JP); Kozo Nogi, Himeji (JP); Kunihiko Ishizaki, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 941 days.

(21) Appl. No.: 16/956,103

(22) PCT Filed: Dec. 21, 2018

(86) PCT No.: PCT/JP2018/047195
§ 371 (c)(1),
(2) Date: Jun. 19, 2020

(87) PCT Pub. No.: WO2019/124536
PCT Pub. Date: Jun. 27, 2019

(65) Prior Publication Data
US 2021/0100684 A1    Apr. 8, 2021

(30) Foreign Application Priority Data

Dec. 21, 2017  (JP) .................. 2017-245273

(51) Int. Cl.
*B01J 20/26* (2006.01)
*A61F 7/03* (2006.01)
*A61F 7/02* (2006.01)

(52) U.S. Cl.
CPC ...... *A61F 7/034* (2013.01); *A61F 2007/0222* (2013.01); *A61F 2007/038* (2013.01)

(58) Field of Classification Search
CPC ................ B01J 20/261; B01J 20/28004; B01J 20/28011
See application file for complete search history.

(56) References Cited

U.S. PATENT DOCUMENTS

| 5,610,208 A | 3/1997 | Dairoku et al. |
| 5,981,070 A | 11/1999 | Ishizaki et al. |

(Continued)

FOREIGN PATENT DOCUMENTS

| CN | 103459473 A | 1/2003 |
| CN | 103459473 A | 12/2013 |

(Continued)

OTHER PUBLICATIONS

Modern Superabsorbent Polymer Technology (1988), Applications of Superabsorbent Polymers, Fredric L. Buchholz, pp. 251-272.

(Continued)

*Primary Examiner* — Robert C Boyle
(74) *Attorney, Agent, or Firm* — Dickinson Wright PLLC

(57) ABSTRACT

An object of the present invention is to provide a water absorbent resin powder for a heat-generating element composition, which suppresses the generation of the aggregates derived from the water absorbent resin and the adhesion of the water absorbent resin in the production of a heat-generating element composition.
A present inventive water absorbent resin powder for a heat-generating element composition includes polyacrylic acid (salt)-based water absorbent resin powder which have a bulk specific gravity (specified by JIS K3362) of 0.630 g/cm³ or less, fluid retention capacity without load (CRC) for a 0.9% by weight aqueous solution of sodium chloride (Continued)

(specified by ERT441.01-2) of 32.0 g/g or less, a weight-average particle diameter (specified by sieve classification) of 250 μm or more, and an amount of a residual glycidyl-based crosslinking agent of 10 ppm or less.

8 Claims, 1 Drawing Sheet

(56) References Cited

U.S. PATENT DOCUMENTS

| | | | |
|---|---|---|---|
| 6,562,879 B1 | 5/2003 | Hatsuda et al. | |
| 2002/0013394 A1 | 1/2002 | Dairoku et al. | |
| 2003/0092849 A1 | 5/2003 | Dairoku et al. | |
| 2006/0025536 A1 | 2/2006 | Dairoku et al. | |
| 2007/0068508 A1 | 3/2007 | York-Leung Wong | |
| 2011/0313113 A1* | 12/2011 | Sakamoto | C08F 20/10 526/318.41 |
| 2012/0258851 A1 | 10/2012 | Nakatsuru et al. | |
| 2013/0026412 A1* | 1/2013 | Machida | B29B 9/16 525/384 |
| 2013/0101851 A1 | 4/2013 | Takaai et al. | |
| 2014/0031473 A1 | 1/2014 | Nogi et al. | |
| 2014/0276516 A1* | 9/2014 | Dagher | A61F 13/537 604/377 |
| 2014/0296465 A1 | 10/2014 | Sakamoto et al. | |
| 2015/0259494 A1 | 9/2015 | Takaai et al. | |
| 2016/0236803 A1* | 8/2016 | Torii | B65B 1/22 |
| 2016/0332141 A1 | 11/2016 | Machida et al. | |

FOREIGN PATENT DOCUMENTS

| | | |
|---|---|---|
| CN | 106726165 A | 5/2017 |
| JP | H02119934 A | 5/1990 |
| JP | H03162479 A | 7/1991 |
| JP | H07278225 A | 10/1995 |
| JP | 2000302876 A | 1/2000 |
| JP | 2000302876 A | 10/2000 |
| JP | 2002060741 A | 2/2002 |
| JP | 2004026904 A | 1/2004 |
| JP | H07278225 A | 1/2007 |
| JP | 2007029131 A | 2/2007 |
| JP | 2010233947 A | 10/2010 |
| JP | 2011063810 A | 1/2011 |
| JP | 2011063810 A | 3/2011 |
| JP | 5264850 B2 | 8/2013 |
| JP | 2015144729 A | 8/2015 |
| WO | 9703114 A1 | 1/1997 |
| WO | WO9703114 A1 | 1/1997 |
| WO | 2010095427 A1 | 8/2010 |
| WO | WO2011126079 A1 | 1/2011 |
| WO | 2011126079 A1 | 10/2011 |
| WO | WO 2011/126079 * | 10/2011 |
| WO | 2014021388 A1 | 2/2014 |

OTHER PUBLICATIONS

Masuda, Fusayoshi "High Water Absorbent Polymer, Polymer New Material, One Point-4", edited by The Society of Polymer Science: Kyoritsu Shuppan Co., Ltd., pp. 81-110, including partial English translation.

Edana, European Disposables and Nonwovens Association, Edana Recommended Test Methods (2002).

Chinese Office Action dated Jan. 6, 2021, which issued in the corresponding Chinese Patent Application No. 201880082282.0, including English translation.

* cited by examiner

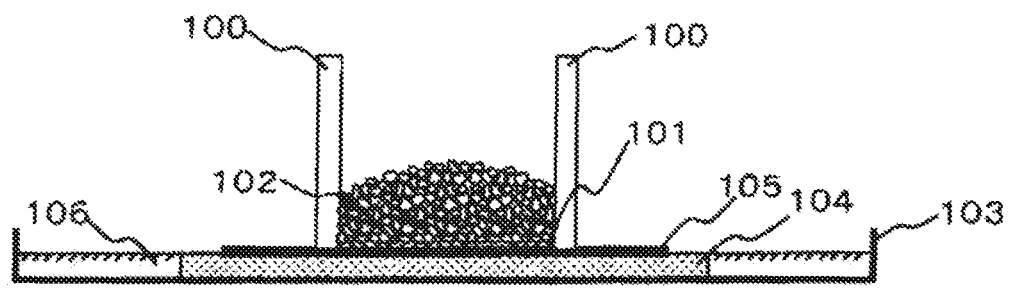

WATER ABSORBENT RESIN POWDER FOR HEAT-GENERATING ELEMENT COMPOSITION, AND HEAT-GENERATING ELEMENT COMPOSITION

TECHNICAL FIELD

The present invention relates to a water absorbent resin powder for a heat-generating element composition, to a heat-generating element composition containing the water absorbent resin powder, and to use of the water absorbent resin powder in a heat-generating element composition.

BACKGROUND ART

A water absorbent resin (another name: Superabsorbent Polymer, abbreviation: SAP) that absorbs a large amount of water to be swollen and gelled is used mainly for hygienic materials such as a disposable diaper, a sanitary napkin, and an incontinence pad. The water absorbent resin is, with use of its high water absorbability, moisture retention capability, and moisture absorbency, also used for many other applications such as a water retention material for greening, a sustained-release gelling agent (e.g., a deodorant), a gelling agent for civil engineering (a water retention material for cement and an H-steel drawing agent), food use, a toy, a sensor, and a cable water sealant (for example, Non-Patent Documents 1 and 2).

One of the applications of the water absorbent resin is a heat-generating element composition, for example, a disposable heat-generating tool and a chemical pocket warmer (for example, a disposable pocket warmer). A composition obtained by mixing a mixture containing activated carbon, a water retention agent, and an aqueous alkali metal salt solution (particularly a high-concentration salt water, for example, a 10% aqueous solution of sodium chloride) with a metal powder (for example, an iron powder) is usable as a heat-generating element composition such as a chemical pocket warmer (hereinafter, the chemical pocket warmer is sometimes referred to as a "pocket warmer") due to heat generation through oxidation of the metal powder in the air. The activated carbon is an oxygen enriching agent for the oxidation of the metal powder, and the aqueous alkali metal salt solution has a function of promoting the oxidation of the metal powder. The heat-generating element composition, for example, a chemical pocket warmer composition enclosed in a breathable bag, has been conventionally and widely used for chemical pocket warmers and other applications. Specific examples of the other applications, similar to or equivalent with the chemical pocket warmer, include insoles, masks, belts, warm eye masks, facial masks, supporters, and foot warmers. For example, as the water retention agent for the aqueous alkali metal salt solution used in the heat-generating element composition such as a chemical pocket warmer, materials having a water retention property, such as a fiber powder, a wood powder, silica gel, and a mineral, have been used. In recent years, the water absorbent resin is used as the water retention agent (a hydrogelling agent for the aqueous alkali metal salt solution) and thus, the heat-generating element composition such as a chemical pocket warmer contains activated carbon, a metal powder, and a hydrogel formed by an aqueous alkali metal salt solution-containing water absorbent resin (for example, Patent Documents 1 to 8). Patent Documents 1 to 3 and 5 propose a water absorbent resin for a chemical pocket warmer, the water absorbent resin for a chemical pocket warmer specified with respect to physical properties such as a particle diameter, water absorption capacity under load, water absorption capacity, and residual monomers. Patent Documents 6 to 8 propose a specific cationic or nonionic crosslinked polymer as the water absorbent resin for a chemical pocket warmer.

The physical properties and the polymer structure (repeating unit) of the water absorbent resin are controlled according to the purpose or the application of the water absorbent resin. For example, even general basic physical properties of the water absorbent resin are known to include a dozen types of physical properties such as water absorption capacity, water absorption capacity under load, a water-soluble content, pH, particle size, a dust amount, powder flowability, bulk specific gravity, and a water content (Non-Patent Document 3). Further, proposed for the water absorbent resin mainly used for hygienic materials are several tens of new parameter physical properties (parameter patents) such as liquid permeability (SFC and GBP) and an anti-caking property, combinations of these properties, and a new polymer structure of the water absorbent resin (Patent Documents 9 to 15).

PRIOR ART DOCUMENTS

Patent Documents

Patent Document 1: JP-A-2004-26904
Patent Document 2: JP-A-2011-63810
Patent Document 3: JP-A-2015-144729
Patent Document 4: JP-A-2007-029131
Patent Document 5: JP-A-2010-233947
Patent Document 6: JP-A-1102-119934
Patent Document 7: JP-A-2002-60741
Patent Document 8: JP-A-1103-162479
Patent Document 9: JP-A-2000-302876
Patent Document 10: WO 2011/126079 A
Patent Document 11: WO 2010/095427 A
Patent Document 12: WO 97/03114 A
Patent Document 13: JP-A-1107-278225
Patent Document 14: WO 2014/021388 A
Patent Document 15: JP 5264850 B

Non-Patent Documents

Non-Patent Document 1: Modern Superabsorbent Polymer Technology (1988), page 251-272
Non-Patent Document 2: Masuda, Fusayoshi "High water absorbent Polymer, Polymer New Material, One Point-4", edited by The Society of Polymer Science: Kyoritsu Shuppan Co., Ltd., p 81-110
Non-Patent Document 3: EDANA RECOMMENDED TEST METHODS (2002)

SUMMARY OF THE INVENTION

Problems to be Solved by the Invention

In the production of a heat-generating element composition such as a chemical pocket warmer, a water absorbent resin serving as a water retention agent for an aqueous alkali metal salt solution has an advantage of retaining water for a longer period at a higher rate than other water retention agents such as a fiber powder, a wood powder, and silica gel do. However, due to high water absorbency, water absorbing rate, and stickiness of the water absorbent resin, when conventional water absorbent resin powders for pocket warmers described in Patent Documents 1 to 8 and the like are used as the water retention agent in the production of the heat-generating element composition such as a chemical pocket warmer, various production-related problems have occurred, such as generation of aggregates formed by adhesion of particles of a gelled water absorbent resin powder and adhesion of a gelled water absorbent resin powder to production equipment such as a vessel for preparing the heat-generating element composition such as a chemical pocket warmer, when the water absorbent resin powder is mixed with the aqueous alkali metal salt solution (particularly a high-concentration aqueous alkali metal salt solution). A main application of the water absorbent resin is hygienic materials such as a disposable diaper among a number of applications of the water absorbent resin. And the water absorbent resin designed for the hygienic materials does not always exhibit suitable performance in other applications and therefore, the fact has been that the performance and the polymer structure of the water absorbent resin are designed each time according to the application of the water absorbent resin.

The present invention has been attained focusing on the circumstances described above, and an object of the present invention is to provide a water absorbent resin powder for a heat-generating element composition, among a number of applications of the water absorbent resin, preferably a water absorbent resin powder for a chemical pocket warmer, which suppresses the generation of the aggregates derived from the water absorbent resin and the adhesion of the water absorbent resin in the production of a heat-generating element composition, such as a chemical pocket warmer, and which has good handleability and high safety. Another object of the present invention is to provide a heat-generating element composition, preferably a chemical pocket warmer composition, which contains the water absorbent resin powder for a heat-generating element composition, preferably the water absorbent resin powder for a chemical pocket warmer, and to provide use of the water absorbent resin powder in a heat-generating element composition, preferably in a chemical pocket warmer.

Means for Solving the Problems

A present inventive water absorbent resin powder for a heat-generating element composition includes polyacrylic acid (salt)-based water absorbent resin powder which have a bulk specific gravity (specified by JIS K3362) of 0.630 g/cm$^3$ or less, fluid retention capacity without load (CRC) for a 0.9% by weight aqueous solution of sodium chloride (specified by ERT441.01-2) of 32.0 g/g or less, a weight-average particle diameter (specified by sieve classification) of 250 μm or more, and an amount of a residual glycidyl-based crosslinking agent of 10 ppm or less.

The present inventive water absorbent resin powder for a heat-generating element composition preferably includes the polyacrylic acid (salt)-based water absorbent resin powder which have permeability dependent absorption under pressure (PDAUP) (specified by WSP 243.3 (10)) of 6.0 g/g or more and/or a 2-min water retainability DW against 10% by weight aqueous solution of sodium chloride of the waster absorbent resin powder of 8.0 g/g or more.

The present invention includes a use of the polyacrylic acid (salt)-based water absorbent resin powder for a heat-generating element composition and also the heat-generating element composition contains activated carbon, the water absorbent resin and an aqueous alkali metal salt solution.

The present invention also includes a heat-generating element composition and also the heat-generating element composition contains the water absorbent resin powder, activated carbon; and an aqueous alkali metal salt solution.

The present invention further preferably includes the case that the heat-generating element composition is a chemical pocket warmer.

Effects of the Invention

According to the present invention, even numerous applications of the water absorbent resin, a dozen basic physical properties of the water absorbent resin, and numerous parameter physical properties of the water absorbent resin, the polyacrylic acid (salt)-based water absorbent resin can be, for use in a heat-generating element composition, preferably in a chemical pocket warmer, controlled to fall in a specific range, with respect to four physical properties (bulk specific gravity, a weight-average particle diameter, water absorption capacity without load, and a residual glycidyl-based crosslinking agent of the water absorbent resin powder), to provide a water absorbent resin powder for a heat-generating element composition, preferably a water absorbent resin powder for a chemical pocket warmer, which is capable of more sufficiently suppressing the aggregation, the adhesion, and the like during mixing with an aqueous alkali metal salt solution than the conventional water absorbent resin powders do in the production of the heat-generating element composition, preferably the chemical pocket warmer, and which has good handleability and high safety. According to the present invention, it is also possible to provide a heat-generating element composition, preferably a chemical pocket warmer composition, which contains the water absorbent resin powder, and to provide use of the water absorbent resin powder in a heat-generating element composition, preferably in a chemical pocket warmer.

BRIEF DESCRIPTION OF THE DRAWING

FIG. 1 is a schematic view of a method for measuring water retainability DW in EXAMPLES.

MODE FOR CARRYING OUT THE INVENTION

Hereinafter, the present invention is described in detail. The present invention, however, is not limited to the following embodiments, but can be carried out with appropriate modifications to the extent that the intent of the present invention is not impaired.

[1] Definition of Terms (1-1) "Water Absorbent Resin"

A "water absorbent resin" in the present invention means a water-swellable and water-insoluble polymer gelling agent. The "water-swellable" means having a CRC (water absorption capacity without load) specified by ERT441.2-02 (2002) of 5 [g/g] or more, and the "water-insoluble" means having an Ext (water-soluble content) specified by ERT470.2-02 (2002) of 50% by weight or less.

The water absorbent resin is appropriately designable and is not particularly limited. The water absorbent resin, however, is preferably a hydrophilic crosslinked polymer obtained by crosslinking and polymerizing an unsaturated monomer having a carboxyl group. The water absorbent resin is not limited to a fully (100% by weight) polymer, but may also be a surface-crosslinked resin or a composition containing an additive or the like, to the extent that the water absorbent resin maintains the performance described above.

In the present invention, the water absorbent resin is obtained by grinding the hydrophilic crosslinked polymer into a powder, and is sometimes, for convenience, referred to as "water absorbent resin particles" when the water absorbent resin has not yet been surface-treated or surface-crosslinked and referred to as a "water absorbent resin powder" when the water absorbent resin has been surface-treated or surface-crosslinked. Further, the "water absorbent resin" collectively refers to even the water absorbent resins obtained in steps and having different shapes (examples of the shapes include a sheet shape, a fiber shape, a film shape, and a gel shape) and even the water absorbent resin composition containing an additive or the like.

(1-2) "Polyacrylic Acid (Salt)"

A "polyacrylic acid (salt)" in the present invention means a polymer containing a graft component optionally and containing 10% by mole or more of acrylic acid and/or a salt thereof (hereinafter, referred to as an "acrylic acid (salt)") as a repeating unit, particularly a polymer containing the acrylic acid (salt) as a main component. The "main component" refers to a content (use amount) of the acrylic acid (salt) of usually 50 to 100% by mole, preferably 70 to 100% by mole, more preferably 90 to 100% by mole, further preferably substantially 100% by mole, relative to all the monomers (exceptan internal crosslinking agent) used for polymerization. When containing a polyacrylic acid salt as the polymer, the water absorbent resin contains, as a counter cation, essentially a water-soluble salt, preferably a monovalent salt as a main component of a neutralized salt, more preferably an alkali metal salt or an ammonium salt, further preferably an alkali metal salt, particularly preferably a sodium salt.

(1-3) "EDANA" and "ERT"

"EDANA" is an abbreviation for European Disposables and Nonwovens Associations, and "ERT" is an abbreviation for EDANA Recommended Test Methods that are methods for measuring a water absorbent resin as European standards (almost international standards) (specifying methods for measuring a dozen basic physical properties). In the present invention, unless otherwise specified, the measurement is performed in accordance with Non-Patent Document 3, the original text of ERT (known document: revised in 2002 or published in 2005). The water absorbent resin powder of the present invention can also be similarly measured in accordance with the original text of ERT.

(a) "CRC" (ERT441.2-02)

"CRC" is an abbreviation for Centrifuge Retention Capacity and means water absorption capacity without load of the water absorbent resin (hereinafter, sometimes also referred to as "water absorption capacity", and equivalent to "absorption capacity"). Specifically, the CRC is water absorption capacity (unit: [g/g]) obtained after 0.200 g of the water absorbent resin in a nonwoven bag is immersed (free swell) in a large excess of a 0.9% by weight aqueous solution of sodium chloride for 30 minutes and then dehydrated with a centrifugal separator.

(b) "AAP" (ERT442.2-02)

"AAP" is an abbreviation for Absorbency Against Pressure and means water absorption capacity under load of the water absorbent resin. Specifically, the AAP is water absorption capacity (unit: [g/g]) obtained after 0.900 g of the water absorbent resin is swollen in a large excess of a 0.9% by weight aqueous solution of sodium chloride for 1 hour under a load of 2.06 kPa (0.3 psi, 21 [g/cm$^2$]). ERT442.2-02 uses the expression Absorption Under Pressure, which, however, has substantially the identical contents with the contents of the AAP. The AAP is sometimes measured by changing the load conditions to 4.83 kPa (0.7 psi, 50 [g/cm$^2$]).

(c) "Ext" (ERT470.2-02)

"Ext" is an abbreviation for Extractables and means a water-soluble content (amount of water-soluble component). Specifically, the Ext is the amount of a dissolved polymer (unit: % by weight) obtained after 1.000 g of the water absorbent resin is added to 200 ml of a 0.9% by weight aqueous solution of sodium chloride and stirred for 16 hours. The amount of the dissolved polymer is measured by pH titration.

(d) "PSD" (ERT420.2-02)

"PSD" is an abbreviation for Particle Size Distribution and means a particle size distribution of the water absorbent resin measured by sieve classification. The weight-average particle diameter (D50) and the particle size distribution width of the water absorbent resin are measured by a method similar to "(1) Average Particle Diameter and Distribution of Particle Diameter" described in the specification of EP 0349240 B, p. 7, lines 25-43.

(e) "Moisture Content" (ERT430.2-02)

"Moisture Content" means a water content of the water absorbent resin. Specifically, the moisture content is a value (unit: % by weight) calculated from drying loss of the water absorbent resin when 1 g of the water absorbent resin is dried at 105° C. for 3 hours. The drying temperature may be changed to 180° C. The water content of a hydrogel crosslinked polymer can be measured by changing the amount of the sample to 2 g, the drying temperature to 180° C., and the drying time to 16 hours. Further, a value calculated by {100−water content (% by weight)} is defined as a "resin solid content" in the present invention and is applicable to both the water absorbent resin and the hydrogel crosslinked polymer.

(1-4) "Liquid Permeability"

"Liquid permeability" in the present invention refers to flowability of a liquid that passes through particles of a swollen gel under load or without load. Typical measurement methods for the liquid permeability include SFC (Saline Flow Conductivity) and GBP (Gel Bed Permeability). PDAUP (Permeability Dependent Absorption Under Pressure) is also measurement for evaluating the liquid permeability.

(1-5) Diffuse Water Absorption Capacity Under Load "PDAUP" (WSP243.3 (10))

"PDAUP" is a measurement method additionally specified in the 2005 revised version of EDANA, is an abbreviation for Permeability Dependent Absorption Under Pressure, and means permeability dependent absorption under pressure of the water absorbent resin. Specifically, the PDAUP refers to water absorption capacity (unit: [g/g]) obtained after 5.0 g of the water absorbent resin is swollen in a large excess of a 0.9% by weight aqueous solution of sodium chloride for 1 hour under a load of 4.83 kPa (49 g/cm$^2$, 0.7 psi).

(1-6) "Bulk Specific Gravity" (JIS K3362)

"Bulk specific gravity" refers to weight (unit: [g/cm$^3$]) of the water absorbent resin obtained when 100 g of the water absorbent resin is charged into a device of JIS K3362 and allowed to freely fall into a 100-mL vessel and thus to fill the vessel. EDANA also specifies the bulk specific gravity of the water absorbent resin by ERT460.2-02.

(1-7) Water Retainability "DW"

"DW" is an abbreviation for Demand Wettability and is, in the present invention, specified as a new index (parameter) appropriate for the production of the water absorbent resin powder for a heat-generating element composition such as a chemical pocket warmer. A "2-min high-concentration salt water DW" means water absorption capacity for high-concentration salt water (a typical example of an aqueous alkali metal salt solution used in a heat-generating element composition such as a chemical pocket warmer) without load for 2 minutes. Specifically, the "2-min high-concentration salt water DW" refers to water absorption capacity (unit: g/g) obtained, similarly to the measurement of the AAP, after 1.0 g of the water absorbent resin, uniformly sprayed to a cylindrical cell having a mesh on the bottom surface, brought into contact with a 10% by weight aqueous solution of sodium chloride for 2 minutes for free swell. The details of the measurement method are described in the item of EXAMPLES.

(1-8) Glycidyl-Based Crosslinking Agent

A glycidyl-based crosslinking agent is a crosslinking agent having one or more epoxy groups, preferably glycidyl groups among a plurality of functional groups. Examples of the crosslinking agent having one epoxy group among a plurality of functional groups include glycidol having a hydroxy group as another functional group. Examples of the crosslinking agent having a plurality of epoxy groups (glycidyl groups), namely a polyepoxy crosslinking agent (polyglycidyl-based crosslinking agent) include ethylene glycol diglycidyl ether.

(1-9) Others

In the present specification, the range "X to Y" means "X or more and Y or less". The weight unit "t (ton)" means "Metric ton", and unless otherwise noted, "ppm" means "ppm by weight". In addition, "weight" and "mass", "% by weight" and "% by mass", and "part by weight" and "part by mass" are each regarded as the same meaning. Further, "acid (salt)" means "acid and/or a salt thereof", and "(meth) acrylic" means "acrylic and/or methacrylic".

[2] Water Absorbent Resin Powder for Heat-Generating Element Composition Such as Chemical Pocket Warmer The water absorbent resin powder of the present invention for a heat-generating element composition such as a chemical pocket warmer is a polyacrylic acid (salt)-based water absorbent resin powder. The water absorbent resin powder has a bulk specific gravity (specified by JIS K3362) of 0.630 g/cm$^3$ or less, fluid retention capacity without load (CRC) (specified by ERT441.01-2) of 32.0 g/g or less, a weight-average particle diameter (specified by sieve classification) of 250 μm or more, and an amount of a residual glycidyl-based crosslinking agent of 10 ppm or less. For the heat-generating element composition such as a chemical pocket warmer, the water absorbent resin powder of the present invention contains a polyacrylic acid (salt) selected as a polymer structure, and is appropriately controlled with respect to four properties (bulk specific gravity, water absorption capacity without load, an average particle diameter, and 10 ppm or less of a residual glycidyl-based crosslinking agent). Due to the polyacrylic acid (salt) and the four physical properties, the water absorbent resin powder has excellent safety and is, regardless of having a low water absorption capacity (low CRC) for a 0.9% by weight aqueous solution of sodium chloride, capable of rapidly absorbing and retaining an aqueous alkali metal salt solution (particularly high-concentration salt water, for example, a 10% by weight aqueous solution of sodium chloride) when mixed with the aqueous alkali metal salt solution, preferably further with materials such as activated carbon for the heat-generating element composition such as a chemical pocket warmer. The water absorbent resin powder is also capable of suppressing an increase in tackiness caused by its swell or the like and is thus capable of solving the problems such as aggregation and adhesion of the water absorbent resin powder in the production of the heat-generating element composition such as a pocket warmer.

(Difference Between Conventional Techniques and Present Invention)

Among numerous applications of the water absorbent resin (Non-Patent Document 1 describes ten typical applications such as a diaper but describes no pocket warmer) and in a dozen basic physical properties of the water absorbent resin, numerous parameter physical properties of the water absorbent resin, and many polymer structures, the polyacrylic acid (salt)-based water absorbent resin having particularly four physical properties in a specific range has been found to be suitable for the water absorbent resin for a heat-generating element composition, preferably the water absorbent resin for a pocket warmer.

That is, generally, the water absorbent resin is desired to have a high water absorption capacity (CRC), preferably 30 and several g/g or more, but in the present invention, the water absorbent resin having a low water absorption capacity (CRC) has been found to be suitable for the heat-generating element composition, preferably the chemical pocket warmer. The water absorbent resin has various average particle diameters according to the usage. It is proposed that the water absorbent resin for a chemical pocket warmer suitably has an average particle diameter of 10 to 150 μm (Patent Document 1). In the present invention, however, the water absorbent resin, in the specification of the four combined physical properties, has been found to suitably have an average particle diameter of 250 μm or more for the heat-generating element composition, preferably an average particle diameter of 250 μm or more for the pocket warmer.

The water absorbent resin also has various bulk specific gravities according to the production method thereof. A water absorbent resin for hygienic materials is proposed that has a high bulk specific gravity, 0.71 g/cm$^3$ or more, from the viewpoints of liquid permeability and physical stability to mechanical damage (Patent Document 9 (JP-A-2000-302876)). Non-Patent Document 2 specifies the measurement results of three kinds of water absorbent resins (samples A to C) as 0.67 g/ml, 0.69 g/ml, and 0.72 g/ml in the bulk specific gravity of EDANA (ERT460.2-02). Patent Document 11 proposes a water absorbent resin for hygienic materials that has a bulk specific gravity of 0.60 to 0.80 g/cm$^3$ (preferably 0.63 to 0.70 g/cm$^3$). In the present invention, however, a water absorbent resin having a low bulk specific gravity (critically 0.630 g/cm$^3$ or less) has been found to be suitable for the heat-generating element composition, preferably for the pocket warmer in the specification of the four combined physical properties.

Further, a water absorbent resin that has less residual monomers is proposed from the viewpoint of safety of the water absorbent resin for a pocket warmer (Patent Document 5). In the meantime, the present invention has focused on a residual glycidyl crosslinking agent from the viewpoint of safety of the water absorbent resin for a heat-generating element composition, preferably safety of the water absorbent resin for a pocket warmer. Patent Document 5 discloses surface crosslinking by a glycidyl-based crosslinking agent in the water absorbent resin for a pocket warmer and examples of the surface crosslinking. The surface crosslinking method in Patent Document 5 is, however, a method similar to comparative examples (more than 10 ppm of a residual glycidyl crosslinking agent) of Patent Documents 12 and 13, and Patent Document 5 does not suggest the residual glycidyl-based crosslinking agent of the present invention (see, for reference, Comparative Example 5 in the present specification described later corresponds to Patent Document 15 which discloses surface crosslinking similar to the crosslinking of Patent Document 5).

Many cationic or nonionic polymer structures are proposed as the water absorbent resin for a pocket warmer (Patent Documents 6 to 8). In the present invention, however, a polyacrylic acid (salt) has been found to be excellent for the heat-generating element composition, particularly the pocket warmer. And the present invention specifies the polyacrylic acid (salt) with respect to the four physical properties (water absorption capacity, bulk specific gravity, an average particle diameter, and a residual glycidyl crosslinking agent) as the water absorbent resin for a heat-generating element composition, preferably the water absorbent resin for a pocket warmer.

Patent Documents 1 to 8 each discloses a water absorbent resin for a pocket warmer, Patent Document 9 discloses, for hygienic materials, a water absorbent resin having a high bulk specific gravity, Patent Document 10 discloses a water absorbent resin attaining both a water absorbing rate (FSR) and the water absorption capacity under load (AAP), Non-Patent Document 1 discloses a number of applications of the water absorbent resin, and Non-Patent Document 2 discloses, as the basic physical properties of the water absorbent resin, a dozen measurement items such as bulk specific gravity (measurement results of 0.67 to 0.72 g/ml). In order to solve the problems focused in the present invention (the adhesion and the aggregation in the production of the heat-generating element composition, preferably the adhesion and the aggregation in the production of the pocket warmer), these conventional techniques disclose no polyacrylic acid (salt)-based water absorbent resin specified by the four physical properties. Patent Documents 1 to 8 disclose a water absorbent resin for a pocket warmer, and Patent Documents 1 to 13 and Non-Patent Documents 1 and 2 describe the four physical properties of the present invention (water absorption capacity, bulk specific gravity, an average particle diameter, and a residual glycidyl crosslinking agent), as well as numerous applications and numerous physical properties of the water absorbent resin, and combinations thereof. In the meantime, the present invention has solved the problems of the present invention by controlling the four physical properties of the water absorbent resin in a specific range, for the heat-generating element composition, preferably the pocket warmer.

(2-1) [Bulk Specific Gravity] (Specified by JIS K3362)

Patent Document 9 (JP-A-2000-302876) and the bulk specific gravity of EDANA (ERT460.2-02) in Non-Patent Document 2 disclose a water absorbent resin having a high bulk specific gravity. In the meantime, in the present invention, a water absorbent resin powder having a low bulk specific gravity has been found to be particularly effective for rapid absorption and retention of an aqueous alkali metal salt solution (particularly high-concentration salt water, for example, a 10% aqueous solution of sodium chloride) in the production of the heat-generating element composition, preferably in the production of the pocket warmer.

Conventional water absorbent resin powders discloses in Patent Documents 1 to 8 and the like are slow at absorbing an aqueous alkali metal salt solution (particularly high-concentration salt water) to cause the water absorbent resin powder to be mixed before sufficiently absorbing the aqueous alkali metal salt solution, so that a surface of the water absorbent resin powder becomes sticky and has high adhesiveness. In the present invention, however, the bulk specific gravity of the water absorbent resin powder can be made lower than those of the conventional water absorbent resin powders to improve the rapid absorption and the retention performance for the aqueous alkali metal salt solution (particularly high-concentration salt water) and to suppress the stickiness of the surface of the water absorbent resin powder. Therefore, it is possible to suppress the aggregation and the adhesion of the water absorbent resin powder attributed to the stickiness on the surface of the water absorbent resin powder.

The water absorbent resin powder exerting such an effect has a bulk specific gravity of 0.630 $g/cm^3$ or less, preferably 0.625 $g/cm^3$ or less, further preferably 0.620 $g/cm^3$ or less. As the bulk specific gravity is lowered, the rapid absorption and the water retainability for the aqueous alkali metal salt solution is improved accordingly, so that the lower limit of the bulk specific gravity is not particularly limited, but is preferably 0.400 $g/cm^3$ or more, more preferably 0.450 $g/cm^3$ or more, further preferably 0.500 $g/cm^3$ or more. The water absorbent resin powder having a bulk specific gravity of less than 0.400 $g/cm^3$ may possibly be easily damaged through a process and lower its physical properties. The water absorbent resin powder having a high bulk specific gravity can be provided by controlling the bulk specific gravity through particle abrasion after drying in Patent Document 9, whereas the water absorbent resin powder of the present invention having a low bulk specific gravity can be provided by adjusting the bulk specific gravity through, for example, foaming polymerization to make the water absorbent resin powder porous, granulation of water absorbent resin particles, and appropriate control of shear conditions in a gel grinding step.

(2-2) [Water Absorption Capacity without Load] (CRC) (Specified by ERT441.01-2)

Conventionally, the water absorbent resin is generally desired to have a high water absorption capacity. In the meantime, in the production of the heat-generating element composition, preferably in the production of the pocket warmer, a low fluid retention capacity without load (CRC) of the water absorbent resin powder for a 0.9% by weight aqueous solution of sodium chloride has been found to be effective for suppressing the aggregation that is generated when the heat-generating element composition, is produced with a high-concentration salt water (for example, a 10% by weight aqueous solution of sodium chloride) and that is attributed to swell on a surface of the water absorbent resin powder.

That is, the use of the water absorbent resin powder having a high fluid retention capacity without load (CRC) for a 0.9% by weight aqueous solution of sodium chloride is seemingly effective for allowing the heat-generating element composition, preferably the chemical pocket warmer to retain therein an aqueous alkali metal salt solution (particularly high-concentration salt water, for example, a 10% by weight aqueous solution of sodium chloride) much more. The water absorbent resin powder having a high water absorption capacity without load (CRC), however, has been found to cause adhesiveness between particles of the water absorbent resin powder to form a large aggregate, as a result of combination of swell of the water absorbent resin powder and stirring power during mixing. On the other hand, in the production of the heat-generating element composition, preferably in the production of the pocket warmer, lowering the water absorption capacity without load (CRC) suppresses the swell accompanying the absorption of the aqueous alkali metal salt solution to enable the water absorbent resin powder to maintain powder's strength and thus to suppress the formation of aggregates or clumping even when stirring power is applied to the water absorbent resin powder during mixing. The water absorbent resin powder exerting such an effect has fluid retention capacity without load (CRC) of 32.0 g/g or less, preferably 31.0 g/g or less, more preferably 30.0 g/g or less, further preferably 29.0 g/g or less. As the fluid retention capacity without load is lowered, the formation of aggregates attributed to the swell can be suppressed accordingly, so that the lower limit of the fluid retention capacity without load is not particularly limited, but is preferably 10.0 g/g or more, more preferably 15.0 g/g or more, further preferably 20.0 g/g or more, from the viewpoint of sufficient retention of the aqueous alkali metal salt solution used for the heat-generating element composition, preferably the aqueous alkali metal salt solution used for the chemical pocket warmer. The CRC of the water absorbent resin powder can be adjusted by appropriately controlling the amount of a crosslinking agent during polymerization and surface crosslinking (secondary crosslinking) following the polymerization.

(2-3) [Weight-Average Particle Diameter] (Specified by Sieve Classification)

Patent Document 1 discloses, as the water absorbent resin for a pocket warmer, a water absorbent resin having an average particle diameter of 20 to 150 µm. In the meantime, in the present invention, the weight-average particle diameter D50 of the water absorbent resin powder has been found to be effective for controlling the aggregation and the adhesion of particularly swollen water absorbent resin powder in the production of the heat-generating element composition, preferably in the production of the pocket warmer.

The water absorbent resin powder having an excessively small average particle diameter (for example, an average particle diameter of 20 to 150 µm described in Patent Document 1) is easily attached to a wall surface of a vessel by a stir during mixing with the aqueous alkali metal salt solution and the like. Further, such a water absorbent resin powder sometimes repels the aqueous alkali metal salt solution to form clumping or allows adhesion of particles of the water absorbent resin powder, to lower uniformity in the particle diameter of the water absorbent resin powder obtained after the mixing. Further, the water absorbent resin powder having an excessively small average particle diameter deteriorates handleability and generates a problem such as generation of dust. On the other hand, appropriate control of the average particle diameter of the water absorbent resin powder enables suppression of the problems such as the aggregation, the adhesion, and the handleability. The water absorbent resin powder exerting such an effect has an average particle diameter of 250 µm or more, preferably 280 µm or more, more preferably 300 µm or more. The upper limit of the average particle diameter is not particularly limited, but is preferably 600 µm or less, more preferably 500 µm or less, further preferably 450 µm or less. The average particle diameter of the water absorbent resin powder can be adjusted by appropriately setting sieving conditions in a grinding step and a classifying step.

(2-4) [Glycidyl-Based Crosslinking Agent]

The glycidyl-based crosslinking agent is, as described above, a crosslinking agent having one or more epoxy groups, preferably glycidyl groups among a plurality of functional groups. Examples of the crosslinking agent having one epoxy group among a plurality of functional groups include glycidol having a hydroxy group as another functional group. Examples of the polyepoxy crosslinking agent (polyglycidyl-based crosslinking agent) having a plurality of epoxy groups (glycidyl groups) include ethylene glycol diglycidyl ether, diethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, sorbitol polyglycidyl ether, pentaerythritol polyglycidyl ether, and trimethylolpropane polyglycidyl ether.

Patent Document 5 discloses, as the water absorbent resin for a chemical pocket warmer, a water absorbent resin having a residual monomer amount of 200 ppm or less from the viewpoint of safety, but does not focus on the residual amount of the glycidyl-based crosslinking agent. The glycidyl-based crosslinking agent is used as an internal crosslinking agent or a surface crosslinking agent in a production process of the water absorbent resin powder and is preferably less contained in the water absorbent resin powder in view of safety during use. Accordingly, the water absorbent resin powder contains (residual) glycidyl-based crosslinking agent of 10 ppm or less relative to the amount (dry basis) of the water absorbent resin powder, preferably a non-detectable (N.D.) level, further preferably unused. When the water absorbent resin powder containing 10 ppm or less of the glycidyl-based crosslinking agent relative to the amount ($dr_y$ basis) of the water absorbent resin powder, together with the aqueous alkali metal salt solution, is used for the heat-generating element composition, preferably for the chemical pocket warmer, together with the aqueous alkali metal solution, the (residual) glycidyl-based crosslinking agent can be diluted with the aqueous alkali metal salt solution to be reduced to the non-detectable (N.D.) level.

The water absorbent resin powder for a heat-generating element composition of the present invention, preferably the water absorbent resin powder for a chemical pocket warmer, simultaneously satisfies the four physical properties in order to solve the problems focused in the present invention (prevention of the aggregation and the adhesion in the production of the heat-generating element composition, preferably in the production of the chemical pocket warmer). In order to improve the effects of the present invention much further, other physical properties of the water absorbent resin powder may also be adjusted. Various types of physical properties, such as liquid permeability, of the water absorbent resin powder may also be appropriately adjusted to the extent that the effects of the present invention are not inhibited.

(2-5) [Water Retention Performance]

(a) [2-Min Water Retainability DW] (Demand Wettability)

In the present invention, the problems have been solved by controlling the four physical properties of the water absorbent resin powder in the specific range, for the heat-generating element composition, preferably for the chemical pocket warmer. Further, the present invention provides a 2-min water retainability DW as a new parameter appropriate for the water absorbent resin for a heat-generating element composition, preferably the water absorbent resin for a chemical pocket warmer.

The new parameter of the present invention, the 2-min water retainability DW of the water absorbent resin powder, is an index indicating water absorbability of the water absorbent resin for a heat-generating element composition, preferably the water absorbent resin for a chemical pocket warmer, for high-concentration salt water in a short time. The water absorbent resin powder having a low 2-min water retainability DW is sometimes mixed before sufficiently absorbing water, to increase stickiness of a mixture or increase the adhesion amount to a vessel. Accordingly, the water absorbent resin powder has a 2-min water retainability DW of preferably 8.0 g/g or more, more preferably 8.5 g/g or more, and preferably 15.0 g/g or less, more preferably 12.0 g/g or less. The 2-min DW of the water absorbent resin powder can be adjusted by appropriately controlling the bulk specific gravity of the water absorbent resin powder.

Mixing of the water absorbent resin powder having a low DW with the aqueous alkali metal salt solution (particularly high-concentration salt water) possibly increases stickiness on a surface of the water absorbent resin powder, make the water absorbent resin powder adheres to a wall surface of a mixing vessel and make particles of the water absorbent resin powder adhering to the wall surface to adhere to each other and aggregate. On the other hand, when the water absorbent resin powder is even improved in the DW and still has fluid retention capacity without load (CRC) of higher than 32 g/g, swelling a surface of the water absorbent resin powder increases stickiness, and decreases strength of the water absorbent resin powder, which possibly lowers mixability of the water absorbent resin powder with activated carbon or the like.

(b) [PDAUP] (Specified by WSP 243.3 (10))

The PDAUP is permeability dependent absorption under pressure under the conditions described above (for a 0.9% by weight aqueous solution of sodium chloride, under a load condition of 4.83 kPa, and with 5.0 g of the water absorbent resin in the measurement). The AAP described later is water absorption capacity obtained under the conditions of a load of 4.83 kPa and 0.9 g of the water absorbent resin in the specification of the prescribed four combined physical properties.

A low PDAUP means a low liquid permeability. In the present invention, the PDAUP of the water absorbent resin powder satisfying the configurations described above is desired to set at preferably 6.0 g/g or more, more preferably 10.0 g/g or more, further preferably 15.0 g/g or more, and preferably 40.0 g/g or less, more preferably 35.0 g/g or less, further preferably 30.0 g/g or less. The physical properties of the water absorbent resin powder, the water absorption capacity without load (CRC) and the liquid permeability (PDAUP) are correlated with each other. The water absorbent resin powder having a high water absorption capacity without load (CRC) tends to decrease the liquid permeability. Therefore, as in, for example, Comparative Example 5 indicated in present EXAMPLES, the water absorbent resin powder having even a CRC of 32.0 g/g or less and a low liquid permeability (PDAUP) is sometimes incapable of allowing the aqueous alkali metal salt solution spread into the entire prepared composition obtained by the mixing and of forming a good mixed state. On the other hand, the water absorbent resin powder satisfying the CRC and the like and the PDAUP described above has an excellent relationship between the water absorption capacity without load (CRC) and the liquid permeability (PDAUP) to be capable of allowing the aqueous alkali metal salt solution spread into the entire prepared composition and thus giving a good mixed state as indicated in Example 1. The PDAUP of the water absorbent resin powder can be adjusted by appropriately controlling the CRC and uniformly performing surface crosslinking (secondary crosslinking) on surfaces of the water absorbent resin particles.

[3] Additional Physical Properties

The water absorbent resin powder of the present invention preferably further satisfies the following physical properties. The water absorbent resin powder satisfying each of the following physical properties much further increases the effects of the present invention.

AAP (Water Absorption Against Pressure) (ERT442.2-02)

The water absorbent resin powder obtained in the present invention has an AAP (water absorption capacity under load (for a 0.9% by weight aqueous solution of sodium chloride, under a load condition of 4.83 kPa, and with 0.9 g of the water absorbent resin in the measurement)), and the AAP under a load of 4.8 kPa of preferably 20 [g/g] or more, more preferably 22 [g/g] or more, further preferably 24 [g/g] or more. The PDAUP described above is water absorption capacity obtained under the condition of a load condition of 4.83 kPa and 5.0 g of the water absorbent resin in the measurement.

The upper limit value of the AAP is not particularly limited, but is preferably 35 [g/g] or less, more preferably 30 [g/g] or less, further preferably 28 [g/g] or less, from the viewpoint of balance with the other physical properties. The use of the water absorbent resin powder having an excellent AAP enables suppression of a decrease in water absorption performance of the water absorbent resin powder caused by the own weight of the material for the heat-generating element composition or the chemical pocket warmer in the production of the heat-generating element composition, preferably in the production of the chemical pocket warmer.

The AAP can be improved by surface crosslinking performed after control of particle size, and the surface crosslinking can be performed until the AAP falls in the range described above.

PSD (Particle Size Distribution)

In view of improvement in the physical properties of the water absorbent resin powder obtained in the present invention, classified water absorbent resin particles have a weight-average particle diameter (D50) of preferably 250 to 500 µm, more preferably 280 to 500 µm, further preferably 300 to 450 µm. Fine particles passing through a sieve (JIS standard sieve) with a mesh size of 150 µm are preferably 0 to 25% by weight, more preferably 0 to 15% by weight, further preferably 0 to 10% by weight, relative to the entire water absorbent resin particles. As large particles not passing through a sieve (JIS standard sieve) with a mesh size of 850 µm or more (or 710 µm or more) are contained less, the water absorbent resin powder is better accordingly. Such large particles are preferably 0 to 3% by weight, more preferably 0 to 1% by weight, further preferably 0% by weight, relative to the entire water absorbent resin particles. In the present invention, the proportion of particles having a particle diameter of 150 µm or more and less than 850 µm, further the proportion of particles having a particle diameter of 150 µm or more and less than 710 µm is adjusted to preferably 80% by weight or more, more preferably 90% by weight or more (the upper limit is 100% by weight), relative to the entire water absorbent resin particles. The logarithmic standard deviation ($\sigma\zeta$) of a particle size distribution is preferably 0.20 to 0.50, more preferably 0.25 to 0.50, further preferably 0.25 to 0.45, particularly preferably 0.30 to 0.40.

These particle sizes can be measured by a method similar to "(1) Average Particle Diameter and Distribution of Particle Diameter" described in the specification of EP 0349240 B, p. 7, lines 25-43. The standard sieve (mesh size) used in the particle size measurement may be appropriately added according to the particle size of an element to be measured. For example, sieving may be performed using an additional standard sieve with a mesh size of 710 µm, 600 µm, or the like so as to give an objective average particle diameter. The particle size of the water absorbent resin particles before the surface crosslinking is applied preferably to the water absorbent resin particles after the surface crosslinking, also further to a final product (water absorbent resin powder).

[4] Use in Heat-Generating Element Composition, Preferably Use in Chemical Pocket Warmer The present invention also includes use of the water absorbent resin powder of the present invention in a heat-generating element composition, preferably in a chemical pocket warmer. The heat-generating element composition, preferably the chemical pocket warmer includes activated carbon, the water absorbent resin powder, and an aqueous alkali metal salt solution and further preferably includes a metal powder.

The activated carbon supplies oxygen to the metal powder, and various types of known activated carbon is usable. For example, activated carbon prepared from various types of known raw materials such as a coconut husk, wood, coal, petroleum pitch, and a resin is usable. Various types of commercially available activated carbon are also obviously usable.

The aqueous alkali metal salt solution is a liquid containing a chloride of an alkali metal having a catalytic action for promoting oxidation of the metal powder. The aqueous alkali metal solution is preferably an aqueous sodium chloride solution, an aqueous lithium chloride solution, or an aqueous potassium chloride solution, and is more preferably an aqueous sodium chloride solution. The concentration of the aqueous alkali metal salt solution is not particularly limited, but because the aqueous alkali metal salt solution having a higher concentration has a higher catalytic effect accordingly, the aqueous alkali metal salt solution is high-concentration salt water having a concentration of preferably 1% or more, more preferably 3% or more, further preferably 5% or more, and preferably less than saturated concentration at a use temperature, more preferably 30% or less, further preferably 20% or less. For example, as the aqueous alkali metal salt solution, an aqueous sodium chloride solution having a concentration of 1% or more is usable.

The metal powder is not particularly limited as long as the metal generates heat by oxidation. Various types of known metal powders such as an iron powder and an aluminum powder are usable.

[5] Heat-Generating Element Composition, Preferably Chemical Pocket Warmer Composition The heat-generating element composition, preferably the chemical pocket warmer composition may contain the materials described above, that is, the water absorbent resin powder of the present invention (preferably the water absorbent resin powder satisfying the DW and/or the PDAUP described above), the activated carbon, and the aqueous alkali metal salt solution. The composition, however, may also contain, as necessary, various types of known additives such as a filler, a surfactant, and vermiculite as a water retention agent other than the water absorbent resin powder. The heat-generating element composition, enclosed by a breathable bag body, such as a nonwoven cloth bag is usable as the heat-generating element composition, preferably the chemical pocket warmer.

The content of each of the materials in the heat-generating element composition, preferably the content of each of the materials in the pocket warmer composition is not particularly limited and may be appropriately adjusted. For example, 0.5 to 10 parts by weight of the activated carbon, 5 to 20 parts by weight of the aqueous alkali metal salt solution, and 10 to 50 parts by weight of the metal powder are usable relative to 1 part by weight of the water absorbent resin powder.

[6] Preparation of Heat-Generating Element Composition, Preferably Preparation of Chemical Pocket Warmer A method for producing a heat-generating element composition, preferably a method for producing a chemical pocket warmer is not particularly limited, and various types of known production methods are employable. For example, activated carbon, the water absorbent resin powder of the present invention, and an aqueous alkali metal salt solution are mixed in advance to prepare a material for the heat-generating element composition, preferably a material for the chemical pocket warmer. The material for the heat-generating element composition, preferably the material for the chemical pocket warmer is mixed with a metal powder. Further, the mixture can be sealed in so as to block out air to give the heat-generating element composition, preferably the chemical pocket warmer.

(Preparation of Material for Heat-Generating Element Composition, Preferably Preparation of Material for Chemical Pocket Warmer)

Various types of known conditions are employable for a mixing ratio and mixing conditions for the activated carbon, the water absorbent resin powder of the present invention, and the aqueous alkali metal salt solution that constitute the material for the heat-generating element composition, preferably the material for the chemical pocket warmer. In the preparation of the material for the heat-generating element composition, preferably the material for the chemical pocket warmer, the use of the water absorbent resin powder of the present invention enables suppression of the various types of problems in mixing such as the formation of aggregates of the water absorbent resin powder and the adhesion of the water absorbent resin powder to an inner wall of a vessel. Therefore, the material for the chemical pocket warmer obtained have high uniformity in the particle diameter and the loss of the material through production process can reduce by using the water absorbent resin powder of the present invention. The chemical pocket warmer containing the material for the chemical pocket warmer is capable of suppressing uneven distribution of heat-generating parts, due to high-uniformity in mixing of the metal powder and the material for the chemical pocket warmer.

The preparation of the material for the heat-generating element composition, preferably the preparation of the material for the chemical pocket warmer, with use of the water absorbent resin powder of the present invention may be performed by mixing the water absorbent resin powder of the present invention with the aqueous alkali metal salt solution, and then adding and mixing the activated carbon in the mixture; by simultaneously mixing the water absorbent resin powder of the present invention, the aqueous alkali metal salt solution, and the activated carbon; or by mixing the water absorbent resin powder of the present invention with the activated carbon, and then adding and mixing the aqueous alkali metal salt solution in the mixture. In the preparation, a known additive may be added and mixed as necessary.

[7] Method for Producing Water Absorbent Resin Powder for Heat-Generating Element Composition, Preferably Method for Producing Water Absorbent Resin Powder for Chemical Pocket Warmer The water absorbent resin powder for a heat-generating element composition of the present invention, preferably the water absorbent resin powder for a chemical pocket warmer may contain a polyacrylic acid (salt) selected as a polymer, and may be controlled to fall in the ranges described above, with respect to the four physical properties (water absorption capacity, bulk specific gravity, a weight-average particle diameter, and a residual glycidyl crosslinking agent). For example, the water absorbent resin powder can be produced by the following production method with appropriate reference to a patent document describing about one or more of the water absorption capacity, the bulk specific gravity, the weight-average particle diameter, or the residual glycidyl crosslinking agent of the water absorbent resin. The method for producing the water absorbent resin powder of the present invention, however, is not limited to the following production method, and any method for producing the water absorbent resin powder having the physical properties described above is employable.

(7-1) Polymerization Step

The present step is a step of polymerizing an aqueous solution mainly containing an acrylic acid (salt) as a raw material (monomer) (hereinafter, sometimes referred to as an "aqueous monomer solution") preferably in a state of an aqueous solution to give a hydrogel crosslinked polymer (hereinafter, sometimes referred to as a "hydrogel").

(Monomer)

The aqueous monomer solution has a concentration of the monomer of preferably 10 to 80% by weight, more preferably 20 to 80% by weight, further preferably 30 to 70% by weight, particularly preferably 40 to 60% by weight.

The hydrogel obtained by the polymerization of the aqueous monomer solution is preferably neutralized in at least a part of acid groups of the polymer in view of the water absorption performance and residual monomers. Such a partially neutralized salt is not particularly limited, but is preferably a monovalent salt selected from an alkali metal salt, an ammonium salt, or an amine salt, more preferably an alkali metal salt, further preferably an alkali metal salt selected from a sodium salt, a lithium salt, or a potassium salt, particularly preferably a sodium salt, in view of the water absorption performance. A basic substance used in the neutralization is not particularly limited, but is preferably a monovalent basic substance such as a hydroxide of an alkali metal (e.g., sodium hydroxide, potassium hydroxide, or lithium hydroxide), or a (hydrogen) carbonate (e.g., sodium (hydrogen) carbonate or potassium (hydrogen) carbonate), more preferably sodium hydroxide.

The neutralization can be performed for each form and state before/during/after the polymerization. For example, a hydrogel obtained by polymerizing unneutralized or low-neutralized (for example, 0 to 30% by mole) acrylic acid can be neutralized or neutralized particularly simultaneously with gel grinding. In view of, for example, productivity and improvement in the physical properties, unpolymerized acrylic acid is preferably neutralized. That is, neutralized acrylic acid (partially neutralized salt of acrylic acid) is preferably used as the monomer.

The percentage of neutralization in the neutralization is not particularly limited, but is, as a final water absorbent resin powder, preferably 10 to 100% by mole, more preferably 30 to 95% by mole, further preferably 45 to 90% by mole, particularly preferably 60 to 80% by mole. The temperature of neutralization is not also particularly limited, but is preferably 10 to 100° C., more preferably 30 to 90° C. As regards other neutralization treatment conditions, the conditions disclosed in EP 574260 B are preferably applied to the present invention. The hydrogel having the percentage of neutralization described above is preferably subjected to gel grinding in the following gel grinding step.

For the purpose of improving the physical properties of the water absorbent resin powder obtained in the present invention, any optional component of water-soluble resins or water absorbent resins such as starch, cellulose, polyvinyl alcohol (PVA), a polyacrylic acid (salt), and polyethyleneimine; various types of foaming agents such as a carbonate, an azo compound, and air bubbles; surfactants; additives; or the like may be added to the aqueous monomer solution, the hydrogel, a dried polymer, the water absorbent resin, or the like in any of production steps of the present invention. As regards the addition amount of these optional components, when a water-soluble resin or a water absorbent resin is added, the total addition amount (the amount of one resin for use of a single resin and the total amount of resins for use of a plurality of resins, the same applies hereinafter) is preferably 0 to 50% by weight, more preferably 0 to 20% by weight, further preferably 0 to 10% by weight, particularly preferably 0 to 3% by weight, relative to the monomer amount. On the other hand, when a foaming agent, a surfactant, or an additive is added, the total amount is preferably 0 to 5% by weight, more preferably 0 to 1% by weight, relative to the monomer amount. The addition of the aqueous solution resin or the water absorbent resin gives a graft polymer or a water absorbent resin composition. These polymers such as a starch-acrylic acid polymer and a PVA-acrylic acid polymer are also regarded as the polyacrylic acid (salt)-based water absorbent resin in the present invention.

Further, from the viewpoints of performance improvement and degradation prevention of the water absorbent resin powder obtained in the present invention, a chelating agent, an α-hydroxycarboxylic compound, or an inorganic reducing agent may also be used. A chelating agent is preferable. The total use amount of these agents or compound is preferably 10 to 5000 ppm, more preferably 10 to 1000 ppm, further preferably 50 to 1000 ppm, particularly preferably 100 to 1000 ppm, relative to the amount of the water absorbent resin powder. The chelating agent is exemplified by the compounds disclosed in U.S. Pat. No. 6,599,989 and WO 2008/090961 A. Preferred are an aminocarboxylic acid-based metal chelating agent, a polyvalent phosphoric acid-based compound, and the chelating agent used in the following examples.

In the present invention, when an acrylic acid (salt) is used as a main component, a hydrophilic or hydrophobic unsaturated monomer(s) (hereinafter, referred to as "other monomer(s)") other than the acrylic acid (salt) may be used in combination. The other monomer(s) is not particularly limited, and is exemplified by methacrylic acid, (anhydrous) maleic acid, 2-(meth)acrylamide-2-methyl prop anesulfonic acid, (meth)acryloxyalkanesulfonic acid, N-vinyl-2-pyrolidone, N-vinylacetamide, (meth)acrylamide, Nisopropyl (meth)acrylamide, N,N-dimethyl(meth)acrylamide, 2-hydroxyethyl(meth)acrylate, methoxy polyethylene glycol (meth)acrylate, polyethyleneglycol(meth)acrylate, stearylacrylate, and salts thereof. The use amount of the other monomer(s) may be appropriately determined to the extent that the water absorption performance of the water absorbent resin powder obtained is not impaired. The use amount is not particularly limited, but the total use amount is preferably 0 to 50% by mole, more preferably 0 to 30% by mole, further preferably 0 to 10% by mole, relative to the weight of all the monomers.

(Internal Crosslinking Agent)

In the present invention, from the viewpoint of the water absorption performance of the water absorbent resin powder obtained, a crosslinking agent (hereinafter, sometimes also referred to as an "internal crosslinking agent") is preferably used. The internal crosslinking agent is not particularly limited, and is exemplified by a crosslinking agent polymerizable with acrylic acid, a crosslinking agent reactive with a carboxyl group, and a crosslinking agent having these properties in combination.

Examples of the polymerizable crosslinking agent include compounds having at least two polymerizable double bonds in a molecule, such as N,N'-methylene bis acrylamide, (poly)ethyleneglycol di(meth)acrylate, (polyoxyethylene)trimethylolpropane tri(meth)acrylate, and a poly(meth)allyloxy alkane. Examples of the reactive crosslinking agent include covalent bonding crosslinking agents such as a polyglycidyl ether (e.g., ethylene glycol diglycidyl ether) and a polyhydric alcohol (e.g., propanediol, glycerin, and sorbitol); and ionic bonding crosslinking agents such as a polyvalent metal compound (e.g., an aluminum salt). Among these crosslinking agents, in view of the water absorption performance, the crosslinking agent polymerizable with acrylic acid is preferable, and an acrylate-based, allyl-based, or acrylamide-based polymerizable crosslinking agent is more preferable. One of these internal crosslinking agents may be used singly. Alternatively, two or more of these internal crosslinking agents may be used in combination. When the polymerizable crosslinking agent and the covalent bonding crosslinking agent are used in combination, the mixing ratio is preferably 10:1 to 1:10.

In view of the physical properties, the use amount of the internal crosslinking agent is preferably 0.001 to 5% by mole, more preferably 0.002 to 2% by mole, further preferably 0.04 to 1% by mole, particularly preferably 0.06 to 0.5% by mole, most preferably 0.07 to 0.2% by mole, relative to the monomer amount except the crosslinking agent. In a particularly preferable embodiment of the present invention, the use amount of the polymerizable crosslinking agent is preferably 0.01 to 1% by mole, more preferably 0.04 to 0.5% by mole, further preferably 0.05 to 0.1% by mole, relative to the monomer amount.

(Polymerization Initiator)

A polymerization initiator may be appropriately selected according to the way of polymerization. The polymerization initiator is not particularly limited, and is exemplified by a photolytic polymerization initiator, a pyrolytic polymerization initiator, and a redox polymerization initiator.

Examples of the photolytic polymerization initiator include a benzoin derivative, a benzyl derivative, an acetophenone derivative, a benzophenone derivative, and an azo compound. Examples of the pyrolytic polymerization initiator include persulfates such as sodium persulfate, potassium persulfate, and ammonium persulfate; peroxides such as hydrogen peroxide, t-butyl peroxide, and methyl ethyl ketone peroxide; and azo compounds such as 2,2'-azobis(2-amidinopropane) dihydrochloride and 2,2'-azobis[2-(2-imidazoline-2-yl)propane] dihydrochloride. Examples of the redox polymerization initiator include a system containing a persulfate or a peroxide, and a reducing compound such as L-ascorbic acid or sodium hydrogen sulfite in combination. A further preferable embodiment is exemplified by combination use of the photolytic polymerization initiator and the pyrolytic polymerization initiator.

The use amount of the polymerization initiator is preferably 0.0001 to 1% by mole, more preferably 0.0005 to 0.5% by mole, relative to the monomer amount. A use amount of the polymerization initiator of more than 1% by mole generates an initiator remaining unreacted, and is not preferable because of a safety and an economic aspect. On the other hand, a use of the polymerization initiator of less than 0.0001% by mole sometimes increases the amount of residual monomers and is thus not preferable.

(Polymerization Method)

The polymerization method applied in the polymerization step is not particularly limited. From the viewpoints of water absorption characteristics, facilitation of polymerization control, and the like, spraying droplet polymerization, aqueous solution polymerization, and reverse-phase suspension polymerization are preferable. Aqueous solution polymerization and reverse-phase suspension polymerization are more preferable. Aqueous solution polymerization is further preferable. Among these types of polymerization, continuous aqueous solution polymerization is particularly preferable. The continuous aqueous solution polymerization may be continuous belt polymerization or continuous kneader polymerization.

Specific examples of the continuous belt polymerization are disclosed in U.S. Pat. Nos. 4,893,999, 6,241,928, and US 2005/215734 A. Specific examples of the continuous kneader polymerization are disclosed in U.S. Pat. Nos. 6,987,151 and 6,710,141. The employment of these types of continuous aqueous solution polymerization improves production efficiency of the water absorbent resin.

One preferable example of the continuous aqueous solution polymerization is high-temperature starting polymerization or high-concentration polymerization. The "high-temperature starting polymerization" refers to a polymerization method for starting polymerization at a temperature of the aqueous monomer solution of preferably 30° C. or more, more preferably 35° C. or more, further preferably 40° C. or more, particularly preferably 50° C. or more (the upper limit is the boiling point). The "high-concentration polymerization" refers to a polymerization method for performing polymerization at a monomer concentration of preferably 30% by mass or more, more preferably 35% by mass or more, further preferably 40% by mass or more, particularly preferably 45% by mass or more (the upper limit is the saturation concentration). These polymerization methods can be combined.

The solid content concentration may be elevated during polymerization. As an index of such elevation of the solid content concentration, the degree of the elevation of the solid content is defined by the following equation.

(Degree of elevation of solid content (% by mass))=
(solid content concentration of polymerized hydrogel (% by mass))−(solid content concentration of aqueous monomer solution (% by mass))

The solid content concentration of the aqueous monomer solution is a value obtained by the following equation. In the equation, the components in the polymerization system are the aqueous monomer solution, the graft component, the water absorbent resin powder, and the additional solid material (for example, water-insoluble fine particles). A hydrophobic solvent in the reverse-phase suspension polymerization is not contained as a component in the polymerization system.

(Solid content of aqueous monomer solution (% by mass))=(mass of (monomer component+graft component+water absorbent resin powder+additional solid material))/(mass of components in polymerization system)×100

The degree of the elevation of the solid content is preferably 1% by mass or more, more preferably 2% by mass or more.

Optionally foaming in the polymerization method is one preferable example of adjustment for a low bulk specific gravity (see, for example, present Examples 4 and 5). Examples of foaming polymerization include a method for adding a foaming agent (for example, a carbonate, a hydrogen carbonate, or an organic solvent) to the aqueous monomer solution as air bubbles introduced into monomers or a polymer; a method for blowing inert gas into the aqueous monomer solution; a method for lowering the solubility of dissolved gas to generate air bubbles derived from the dissolved gas in monomers and dispersing the air bubbles; and a method for generating air bubbles through moisture evaporation during polymerization (particularly boiling polymerization). Further, there is a method for adding a surfactant or a water-soluble polymer (thickener) for stabilizing air bubbles. For example, as the foaming polymerization, WO 2011/078298 A, WO 2010/095427 A, WO 2013/072268 A, WO 2016/204390 A, and the like can be appropriately referred to.

The surfactant (bubble stabilizer), the foaming agent, or the water-soluble polymer (the thickener for stabilizing air bubbles) optionally usable in the foaming polymerization can be appropriately selected. Particularly, the surfactant is suitably used. When the surfactant is used, the use amount thereof is preferably 0 to 1 part by weight, more preferably 0 to 0.1 parts by weight, relative to 100 parts by weight of the solid content of the raw material monomer of the water absorbent resin. The use amount of the foaming agent is preferably 0 to 5 parts by weight, further preferably 0 to 3 parts by weight. The use amount of the water-soluble polymer is preferably 0 to 30 parts by weight, further preferably 0 to 5 parts by weight. The lower limit of the use amount may be 0, preferably 0.01 parts by weight or more. In the foaming polymerization with the foaming agent such as a carbonate (hydrogen carbonate), foaming attributed to the foaming agent occurs during polymerization or drying after the polymerization. Apart from the foaming with the foaming agent, the polymerization may be performed by mixing the optionally used bubble stabilizer, i.e., the surfactant or the water-soluble polymer with a bubble-dispersed aqueous monomer solution into which air bubbles have been introduced. Due to the introduction of air bubbles, the aqueous monomer solution may be polymerized while swollen to a volume of preferably 1.001 to 10 times, more preferably 1.01 to 5 times, further preferably 1.05 to 2 times.

Here, the water absorbent resin powder obtained can be confirmed to be a foamed body by an SEM photograph, porosity, or an internal gas bubble ratio, similarly to granules described later. When the water absorbent resin powder having the bulk specific gravity of the present invention is obtained by the foaming polymerization, the foaming polymerization may be performed so that the pore diameter of a hollow formed on a surface of the water absorbent resin powder is preferably 0.1 to 100 μm, further 1 to 50 μm, particularly 2 to 40 μm.

The polymerization can be performed in an air atmosphere, but is preferably performed in water vapor or in an atmosphere of inert gas such as nitrogen or argon (for example, an oxygen concentration of 1% by volume or less). Further, the polymerization is preferably performed after substitution of dissolved oxygen in monomers or in a monomer-containing solution with inert gas (degassing) (for example, an oxygen of less than 1 [mg/L]). Such degassing is also excellent for stabilization of the monomers to cause no gelling before polymerization and enables provision of the water absorbent resin powder having higher physical properties.

(7-2) Gel Grinding Step

The present step is a step of mincing the hydrogel crosslinked polymer during the polymerization or after the polymerization to give a particulate hydrogel crosslinked polymer (hereinafter, sometimes referred to as a "particulate hydrogel"). The present step is referred to as "gel grinding" to distinguish the present step from "grinding" in the following (7-4) Grinding step and classifying step.

The conventional gel grinding techniques have been, as disclosed in U.S. Pat. Nos. 7,694,900, 6,565,768, 6,140,395, and the like, mainly a technique of giving as less shear force as possible. The present invention is characterized by giving more shear force than the shear force in the conventional techniques and performing shearing until giving the prescribed bulk density. As to an embodiment, execution conditions, and the like of the gel grinding, the gel grinding step is employed, for example, as strong gel grinding. Preferably, in the gel grinding method described in Patent Document 10 (WO 2011/126079 A), the strong gel grinding can be employed with high-level gel grinding energy among the levels of gel-grinding energy (GGE) in Patent Document 10, further under the condition of exceeding the gel grinding energy in Patent Document 10, until the bulk specific gravity satisfies the specification of the present invention, to increase the bulk density of a surface-crosslinked water absorbent resin (for example, see present Examples 1 to 3). Further, for example, appropriate control of grinding conditions such as the die pore diameter of a grinding device (e.g., a meat chopper), the charge amount of the hydrogel, the addition amount of water, the temperature, and the rotation frequency of a screw shaft gives a particulate hydrogel having irregularly broken shape, a desired bulk density, and the like.

Patent Document 10 discloses an influence of the gel grinding energy (GGE) on the water absorbing rate (FSR), but does not describe an influence of the gel grinding energy (GGE) on the bulk specific gravity. In the present invention, it has been found that the bulk specific gravity can be reduced referring to Patent Document 10, and as one example of the method for controlling the bulk specific gravity of the water absorbent resin for a pocket warmer of the present invention (see, for example, present Examples 1 to 3), the gel grinding of Patent Document 10 is applicable to the method for producing the water absorbent resin for a pocket warmer.

(a) Gel Temperature

In view of control of particle size and the physical properties, the temperature (gel temperature) of the hydrogel before the gel grinding is preferably 40 to 120° C., more preferably 60° C. to 120° C., further preferably 60 to 110° C., particularly preferably 65° C. to 110° C. A gel temperature of less than 40° C. sometimes increases hardness of the hydrogel due to the characteristics of the hydrogel to cause trouble controlling the particle shape or the particle size distribution during the gel grinding. On the other hand, a gel temperature of more than 120° C. sometimes increases softness of the hydrogel to cause trouble controlling the particle shape or the particle size distribution. The gel temperature can be appropriately controlled by polymerization temperature, heating after polymerization, warming, cooling, or the like.

(b) Resin Solid Content

From the viewpoint of the physical properties, the resin solid content of the hydrogel before the gel grinding is 10 to 80% by weight, preferably 30 to 80% by weight, more preferably 40 to 80% by weight, further preferably 45 to 60% by weight, particularly preferably 50 to 60% by weight. A resin solid content of less than 10% by weight increases softness of the hydrogel to possibly cause trouble controlling the particle shape or the particle size distribution, and is thus not preferable. Adversely, a resin solid content of more than 80% by weight increases hardness of the hydrogel to possibly cause trouble controlling the particle shape or the particle size distribution, and is thus not preferable. This resin solid content of the hydrogel can be appropriately controlled by, for example, polymerization concentration, moisture evaporation during polymerization, addition of a water absorbent resin fine powder in the polymerization step (fine powder recycling step), or addition of water or partial drying after polymerization as necessary.

The resin solid content before the gel grinding is obtained from drying loss after the hydrogel is cut or fragmented using scissors, a cutter, or the like into a side of 5 mm or less, preferably 1 to 3 mm.

(c) Gel Grinder

The gel grinding device used in the present step is not particularly limited. Examples of the gel grinding device include a gel grinder having a plurality of rotational stirring blades such as a batch-type or continuous double-armed kneader, an extruder, a meat chopper, and particularly a screw extruder.

Preferred example is a screw extruder having a porous plate disposed at one end of a casing of the screw extruder. Such a screw extruder is exemplified by a screw extruder disclosed in JP-A-2000-63527.

(d) Use of Additive

An additive, a neutralizing agent, or the like can be added to the hydrogel and kneaded with the hydrogel. The water absorbent resin obtained in this manner may be modified. Specifically, an aqueous solution containing a basic substance (for example, a 10 to 50% by weight aqueous solution of sodium hydroxide) may be added during the gel grinding to neutralize (particularly in the range of the percentage of the neutralization described above) the hydrogel. Alternatively, a water absorbent resin fine powder (0.1 to 30% by weight (relative to the resin solid content)) may be added for fine powder recycling. Further, a polymerization initiator, a reducing agent, or 0.001 to 3% by weight of a chelating agent (relative to the resin solid content) may also be added to and kneaded with the hydrogel during the gel grinding to reduce the amount of residual monomers and impart endurance.

(7-3) Drying Step

The present step is a step of drying the particulate hydrogel obtained in the gel grinding step to give a dried polymer. Hereinafter, a drying method preferably applied to the present invention is described.

As the drying method in the drying step of the present invention, various drying methods are employed such as drying by heating, hot air drying, drying under reduced pressure, infrared drying, microwave drying, drying by a drum dryer, drying by azeotropic dehydration with a hydrophobic organic solvent, and high-humidity drying using high-temperature water vapor. Preferably employed is hot air drying, more preferably hot air drying with a dew point of 40 to 100° C., further preferably a dew point of 50 to 90° C.

As the drying device used in the drying step, more preferable example of the drying device is a belt dryer. In addition, one or more of a heat transfer conductive dryer, a radiation heat transfer dryer, a hot air heat transfer dryer, a dielectric heating dryer, or the like are usable in combination as necessary. Among these dryers, a hot air heat transfer dryer (hereinafter, referred to as a "hot air dryer") is preferable from the view point of a drying rate. Examples of the type of the hot air dryer include a through-flow belt (band) type, a through-flow circuit type, a vertical through-flow type, a parallel flow belt (band) type, a through-flow tunnel type, a through-flow groove stirring type, a fluidized-bed type, an airflow type, and a spray type. In the present invention, a through-flow belt-type hot air dryer is preferable from the viewpoint of control of the physical properties.

Hereinafter, the drying conditions and the like in the drying step of the present invention are described. Performing the drying under the following drying conditions enables improvement in the liquid permeability of the water absorbent resin powder obtained by surface-treating the dried polymer obtained.

(Drying Temperature)

The drying temperature in the drying step of the present invention (preferably with the through-flow belt dryer) is 100 to 300° C., preferably 150 to 250° C., more preferably 160 to 220° C., further preferably 170 to 200° C. A drying temperature of 100 to 300° C. enables reduction of the drying time. Further, a drying temperature of 100 to 300° C. leads to a tendency of improving the liquid permeability and the water absorbing rate of the water absorbent resin powder obtained. A drying temperature of more than 300° C. may possibly damage a polymer chain to lower the physical properties. A drying temperature of less than 100° C. may possibly give no change in the water absorbing rate, generate an undried polymer, and cause clogging during the subsequent grinding step.

(Drying Time)

The drying time in the drying step of the present invention (preferably with the through-flow belt dryer) depends on the surface area of the particulate hydrogel, the kind of the dryer, or the like, and may be appropriately set so as to give an objective water content. The drying time is preferably 1 minute to 10 hours, more preferably 5 minutes to 2 hours, further preferably 10 to 120 minutes, particularly preferably 20 to 60 minutes.

The duration of time from discharging of the particulate hydrogel discharged out of the gel grinding step to is introducing to the drying step, that is, the time taken for the particulate hydrogel to move from an outlet of the gel grinder to an inlet of the dryer is favorably shorter, preferably within 2 hours, more preferably within 1 hour, further preferably within 30 minutes, particularly preferably within 10 minutes, most preferably within 2 minutes.

(Dew Point of Hot Air)

In the drying step of the present invention, the hot air used in the through-flow belt dryer contains at least water vapor and has a dew point of preferably 30 to 100° C., more preferably 30 to 80° C. Controlling the dew point of the hot air and further preferably the gel particle diameter in the above range enables reduction of the amount of residual monomers and further prevention of a decrease in the bulk specific gravity of the dried polymer. The dew point is a value obtained at the time when the particulate hydrogel has a water content of at least 10% by weight or more, preferably 20% by weight or more.

(Resin Solid Content)

The particulate hydrogel obtained in the gel grinding step is dried in the present drying step to form a dried polymer. The resin solid content calculated from the drying loss (heating 1 g of a powder or particles at 180° C. for 3 hours) of the dried polymer is preferably more than 80% by weight, more preferably 85 to 99% by weight, further preferably 90 to 98% by weight, particularly preferably 92 to 97% by weight.

(7-4) Grinding Step and Classifying Step

The present step is a step of grinding and classifying the dried polymer obtained in the drying step to give water absorbent resin particles. The present step is different from the gel grinding step in the resin solid content during the grinding, particularly in that an object to be ground has undergone the drying step (preferably dried to give the resin solid content described above). The water absorbent resin particles obtained after the grinding step is sometimes also referred to as a ground polymer.

The dried polymer obtained in the drying step is directly usable as the water absorbent resin powder, but is preferably controlled to have a specific particle size for improvement in the physical properties given by a surface treatment step, particularly a surface crosslinking step described later. The control of particle size can be appropriately performed not only by the present grinding step and classifying step, but also by the polymerization step, a fine powder collecting step, a granulation step, or the like. Hereinafter, the particle size is specified by a standard sieve (JIS Z8801-1 (2000)).

The grinder usable in the grinding step is not particularly limited, and is exemplified by a vibration mill, a roll granulator, a knuckle grinder, a roll mill, a high-speed rotation grinder (e.g., a pin mill, a hammer mill, and a screw mill), and a cylindrical mixer. In view of the control of particle size, a roll mill or a roll granulator is preferable.

In the present classifying step, classification operation is performed to give a following particle size. When surface crosslinking is performed, the classification operation is preferably performed before the surface crosslinking step (first classifying step), and the classification operation may also further be performed after the surface crosslinking (second classifying step). The classification operation is not particularly limited, but may be performed, for example, by sieving with a sieve. The particle size distribution (PSD) is adjusted for a preferable one in the range designed for the water absorbent resin for a heat-generating element composition, preferably a pocket warmer before or after the surface crosslinking.

(7-5) Surface Treatment Step

The method for producing the polyacrylic acid (salt)-based water absorbent resin powder according to the present invention preferably further includes a surface treatment step to improve the water absorption performance (water absorbency against pressure, liquid permeability, water absorbing rate, and the like). The surface treatment step includes a surface crosslinking step performed using a known surface crosslinking agent and a known surface crosslinking method, and further includes another component adding step as necessary.

(Covalent Bonding Surface Crosslinking Agent)

The surface crosslinking agent usable in the present invention can be exemplified by various organic or inorganic crosslinking agents, and an organic surface crosslinking agent is preferably usable. From the aspect of the physical properties, preferred as the surface crosslinking agent are a polyhydric alcohol compound, an epoxy compound (glycidyl-based compound), a polyvalent amine compound or a condensate thereof with a halo epoxy compound, an oxazoline compound, a (mono, di, or poly)oxazolidinone compound, and an alkylene carbonate compound. Particularly preferably usable example is a dehydrating reactive crosslinking agent selected from a polyhydric alcohol compound, an alkylene carbonate compound, or an oxazolidinone compound that needs a high-temperature reaction. When the dehydrating reactive crosslinking agent is not used, the surface crosslinking agent can be more specifically exemplified by the compounds described in U.S. Pat. Nos. 6,228,930, 6,071,976, and 6,254,990. Examples of the compounds include polyhydric alcohol compounds such as mono, di, tri, tetra or polypropylene glycol, 1,3-propanediol, glycerin, 1,4-butanediol, 1,3-butanediol, 1,5-pentanediol, 1,6-hexanediol, and sorbitol; epoxy compounds such as ethylene glycol diglycidyl ether and glycidol; alkylene carbonate compounds such as ethylene carbonate; oxetane compounds; and cyclic urea compounds such as 2-imidazolidinone.

(Solvent and the Like)

The use amount of the surface crosslinking agent is preferably about 0.001 to 10 parts by weight, more preferably about 0.01 to 5 parts by weight, relative to 100 parts by weight of the water absorbent resin particles, and is appropriately determined. Water is preferably used together with the surface crosslinking agent. The amount of water to be used is in the range of preferably 0.5 to 20 parts by weight, more preferably 0.5 to 10 parts by weight, relative to 100 parts by weight of the water absorbent resin particles. In combination use of the inorganic surface crosslinking agent and the organic surface crosslinking agent, the use amount of each of the surface crosslinking agents is preferably 0.001 to 10 parts by weight, more preferably 0.01 to 5 parts by weight, relative to 100 parts by weight of the water absorbent resin particles.

In using the surface crosslinking agent, a hydrophilic organic solvent may also be used, and the use amount of the hydrophilic organic solvent is in the range of preferably 0 to 10 parts by weight, more preferably 0 to 5 parts by weight, relative to 100 parts by weight of the water absorbent resin particles. In mixing of the crosslinking agent solution with the water absorbent resin particles, a water-insoluble fine particle powder or a surfactant may be added as well to the extent that the effects of the present invention are not prevented, for example, in an amount of preferably 0 to 10 parts by weight, more preferably 0 to 5 parts by weight, further more preferably 0 to 1 part by weight. The surfactant to be used and the use amount thereof are described in U.S. Pat. No. 7,473,739.

(Mixing)

The water absorbent resin particles are swollen by water and the like in the surface crosslinking agent solution during mixing of the water absorbent resin particles with the surface crosslinking agent solution. The swollen water absorbent resin particles are dried by heating. In the drying, the heating temperature is preferably 80 to 220° C. The heating time is preferably 10 to 120 minutes.

(Residual Glycidyl-Based Crosslinking Agent)

In the present invention, from the viewpoint of safety of the water absorbent resin powder obtained, the residual glycidyl-based crosslinking agent is preferably reduced. One preferable means is that no glycidyl-based crosslinking agent is used as the surface crosslinking agent (see, for example, present Examples 1 to 5). However, when the glycidyl-based crosslinking agent is used, one preferable means of reducing the glycidyl-based crosslinking agent is the method for reducing the residual glycidyl crosslinking agent described in Patent Document 12 (WO 97/03114 A) or Patent Document 13 (JP-A-1107-278225), and the method being specifically simultaneous use of the glycidyl-based crosslinking agent with a residual glycidyl crosslinking agent reducer typified by a polyhydric alcohol, an inorganic acid, or an organic acid; further mixing water after mixing the glycidyl-based crosslinking agent, or combination use with specific surface crosslinking by Patent Document 14 (WO 2014/021388 A) (see, for example, present Example 6). That is, when the water absorbent resin powder of the present invention is surface-crosslinked, no glycidyl-based crosslinking agent is used as the surface crosslinking agent, or surface crosslinking is selected that the residual glycidyl-based crosslinking agent reduces, by the technique described later, to 10 ppm or less, further 5 ppm or less, 3 ppm or less, 1 ppm, particularly ND (non-detectable, detection limit or less, i.e., less than 1 ppm). It is particularly preferred that no glycidyl-based crosslinking agent is used as the surface crosslinking agent, or that the residual glycidyl crosslinking agent is ND. Further preferred is that no glycidyl-based crosslinking agent is used as the surface crosslinking agent.

Patent Document 5 and examples thereof disclose surface crosslinking by a glycidyl-based crosslinking agent in the water absorbent resin for a pocket warmer. The surface crosslinking method in Patent Document 5, however, is a method similar to comparative examples (more than 10 ppm of a residual glycidyl crosslinking agent) of Patent Documents 12 and 13 and examples of Patent Document 15, and Patent Document 5 does not suggest the residual glycidyl-based crosslinking agent disclosed in the present invention. As regards the residual glycidyl crosslinking agent in Patent Document 5, see also Comparative Example 5 described later (the amount of a residual glycidyl crosslinking agent in Patent Document 15 disclosing the residual glycidyl-based crosslinking agent in surface crosslinking similar to the surface crosslinking in Patent Document 5). As understood from Comparative Example 5 described later, neither Patent Document 5 nor 15 suggest the present invention.

(Other Surface Crosslinking Method)

As the surface crosslinking method used in the present invention, a surface crosslinking method using a radical polymerization initiator (U.S. Pat. No. 4,783,510, WO 2006/062258 A) or a surface crosslinking method for polymerizing a monomer on surfaces of the water absorbent resin particles (US 2005/048221 A, US 2009/0239966 A, and WO 2009/048160 A) may be used in place of the surface crosslinking using the surface crosslinking agent described above.

In the surface crosslinking method, the radical polymerization initiator that is preferably used is a persulfate, the monomer that is optionally and preferably used is an acrylic acid (salt) as well as the crosslinking agents described above, and the solvent that is preferably used is water. These compounds are added to surfaces of the water absorbent resin particles, and then an active energy ray (particularly ultraviolet) or heating causes surface crosslinking through crosslinking polymerization or a crosslinking reaction by the radical polymerization initiator on the surfaces of the water absorbent resin particles.

(Ion Bonding Surface Crosslinking Agent)

In the present invention, the production method further includes, simultaneously with or separately from the surface crosslinking step, an adding step of adding any one or more of a polyvalent metal salt, a cationic polymer, and inorganic fine particles. The specific timing of adding these additives is, for example, after the surface crosslinking treatment step, other than the surface crosslinking step. Other than the organic surface crosslinking agent, an inorganic surface crosslinking agent may be used or used in combination to improve the liquid permeability, the water absorbing rate, and the like. The inorganic surface crosslinking agent to be used can be exemplified by a salt (an organic salt or an inorganic salt) and a hydroxide of a polyvalent metal such as a divalent or more, preferably a trivalent or tetravalent metal. Examples of usable polyvalent metals include aluminum and zirconium, and examples include aluminum lactate and aluminum sulfate. Preferred is an aqueous solution containing aluminum sulfate. These inorganic surface crosslinking agent are used simultaneously with or separately from the organic surface crosslinking agent. The surface crosslinking by the polyvalent metal is described in WO 2007/121037 A, WO 2008/09843 A, WO 2008/09842 A, U.S. Pat. Nos. 7,157,141, 6,605,673, 6,620,889, US 2005/0288182 A, US 2005/0070671 A, US 2007/0106013 A, and US 2006/0073969 A.

Further, a cationic polymer, particularly a cationic polymer having a weight-average molecular weight of about 5,000 to 1,000,000 may be used simultaneously or separately to improve the liquid permeability and the like. The cationic polymer to be used is, for example, preferably a vinylamine polymer or the like, and examples of the cationic polymer are described in U.S. Pat. No. 7,098,284, WO 2006/082188 A, WO 2006/082189 A, WO 2006/082197 A, WO 2006/111402 A, WO 2006/111403 A, and WO 2006/111404 A.

Similarly, inorganic fine particles may also be used. For example, silicon dioxide or the like described in U.S. Pat. No. 7,638,570 is preferable.

(7-6) Granulation Step

The production method can include a granulation step after the grinding step and classifying step, or after (7-5) Surface treatment step. The present step is the third method useful for adjustment for a low bulk specific gravity.

In the present invention, the granulation is, as in present Example 6 described later, to attach particles to each other by a physical or chemical technique and thus form larger particles than the original particles. The water absorbent resin particles used in the granulation step of the present invention have a weight-average particle diameter (specified by sieve classification) of preferably 10 µm to 200 µm, further preferably 15 to 180 µm, particularly preferably 20 µm to 180 µm. Regarding to the granulation method, as one example of the granulation method using an aqueous solution as a binder, the method described in U.S. Pat. No. 7,153,910 for granulating by preheating an aqueous liquid and adding the preheated aqueous liquid to the water absorbent resin particles, the method described in JP-A-2015-54151 for granulating with water vapor, or the method described in WO 2009/031701 A for granulating with water vapor and an aqueous liquid are referred to.

The amount of the binder is 0.1 to 200 parts by weight, further 1 to 150 parts by weight, 5 to 120 parts by weight, relative to 100 parts by weight of the water absorbent resin fine powder before the granulation, and is appropriately selected. The added binder (particularly water) may be dried as necessary to give a prescribed solid content (water content), for example, 70% or more, 80% by weight or more in terms of the solid content of granules of the water absorbent resin powder (drying loss after 3 hours at 180° C.). An excessive amount of the binder lowers the water absorbability of the water absorbent resin powder obtained, but a small amount of the binder lowers granule strength.

The fact that the water absorbent resin powder obtained has a granule form can be confirmed by a plurality of fine particles (for example, a weight-average particle diameter of 10 to 200 µm) of the water absorbent resin bound with each other to give a weight-average particle diameter of 250 µm or more of the present invention. The fact can also be confirmed through observation of a surface state by an SEM photograph (confirmation of a binding interface between particles) or analysis of porosity or a bubble ratio. By the granulation of the present invention performed by using a binder (particularly water) as necessary and further drying the binder as necessary, the weight-average particle diameter after the granulation preferably increases 1.1 to 10 times, further 1.2 to 5 times, particularly 1.4 to 4 times relative to the weight-average particle diameter before the granulation. An increase of the average particle diameter through the granulation enables provision of the water absorbent resin having the bulk specific gravity of the present invention (for example, see present Example 6).

The production method of the present invention is preferably a method for producing the water absorbent resin powder, the method including a step of adding any one or more of the polyvalent metal, the cationic polymer, and the inorganic particles described above. These additives are preferably used in combination with the covalent bonding surface crosslinking agent simultaneously or separately.

(7-7) Other Steps (Fine Powder Recycling Step and the Like)

The production method may also include, in addition to the steps described above, a vaporized monomer recycling step, a granulation step, a fine powder removing step, a fine powder recycling step, and the like as necessary. In order to, for example, prevent degradation of the gel, in any part or all of the steps described above, the following additives may be used as necessary. That is, a water-soluble or water-insoluble polymer, a lubricant, a chelating agent, a deodorant, an antibacterial agent, water, a surfactant, water-insoluble fine particles, an antioxidant, a reducing agent or the like can be added and mixed in an amount of preferably 0 to 30% by weight, more preferably 0.01 to 10% by weight, relative to the amount of the water absorbent resin powder. These additives can also be used as a surface treatment agent.

Further, the production method of the present invention can include a fine powder recycling step. The fine powder recycling step refers to a step of separating a fine powder (particularly a fine powder containing 70% by weight or more of a powder having a particle diameter of 150 μm or less) generated in the drying step and in the grinding step and classifying step as necessary, and then recycling the fine powder in the polymerization step or the drying step directly or after hydration. As the fine powder recycling step, the method described in US 2006/247351 A or U.S. Pat. No. 6,228,930 is applicable.

Further, an oxidant, an antioxidant, water, a polyvalent metal compound, water-insoluble inorganic or organic powders such as silica and a metal soap, a deodorant, an antibacterial agent, polymer polyamine, or the like may also be, according to the purpose, added in an amount of 0 to 3% by weight, preferably 0 to 1% by weight to the water absorbent resin powder.

(Applications)

The heat-generating element composition of the present invention generates heat using heat generated by an oxidation reaction of an oxidizable metal such as an iron powder. The heat-generating element composition of the present invention is suitable for particularly a disposable heat-generating tool, further a chemical pocket warmer, so-called a disposable pocket warmer. The heat-generating element composition of the present invention is usable for various types of applications, using generated heat.

The water absorbent resin powder of the present invention is, as a disposable heat-generating tool, appropriately usable for a heat-generating tool similar to the chemical pocket warmer. For example, the heat-generating element composition of the present invention that is contained in a bag-shaped object formed in a desired shape is suitable for warmers such as an insole, a mask, a belt, a warm eye mask, a facial mask (e.g., JP-A-2003-334212), a supporter, and a foot warmer (e.g., JP-A-2003-334211), particularly for warmers for a body. Here, the heat-generating tool suitable for a body is usable for not only a human body but also for an animal body, but is suitably applied to a human body. The heat-generating tool containing the water absorbent resin powder of the present invention is, in addition to the warmers for a body, appropriately usable for articles that need warming or heating, such as a warmer for food (for example, warming or heating of packed meal).

The present application claims priority based on Japanese Patent Application No. 2017-245273 filed on Dec. 21, 2017. All the contents described in Japanese Patent Application No. 2017-245273 filed on Dec. 21, 2017 are incorporated herein by reference.

EXAMPLES

Hereinafter, the invention is described according to examples. The present invention, however, is not to be understood as being limited to the examples. The physical properties described in the claims and the examples of the present invention are, unless otherwise described, obtained according to the EDANA methods and the following measurement methods under the conditions of room temperature (20 to 25° C.) and a humidity of 50% RH. Further, the electric devices described in the examples and comparative examples are used with a power source of 200 V or 100 V, and 60 Hz. The "liter" is sometimes described as "L", and the "% by weight" as "wt %" for convenience.

(a) Weight-Average Particle Diameter (D50)

The weight-average particle diameter (D50) of the water absorbent resin powder was measured with reference to Patent Documents 9 and 10 in accordance with the measurement method described in EP 0349240 B.

(b) Bulk Specific Gravity

The bulk specific gravity of the water absorbent resin powder was measured with reference to Patent Document 11 (WO 2010/095427 A), using a bulk specific gravity measuring device (manufactured by Kabushiki Kaisha Kuramochi Kagaku Kiki Seisakusho), in accordance with JIS K 3362. The water absorbent resin powder in an amount of 100.0 g that had been sufficiently mixed to eliminate a bias in particle size was put into a funnel with damper-closed. Then, the damper was rapidly opened to drop the water absorbent resin powder into a receiver (weight W1 [g]) having an internal capacity of 100 cm$^3$. The water absorbent resin powder heaped on the receiver was levelled off with a glass rod. The weight (weight W2 [g]) of the receiver containing the water absorbent resin powder was accurately measured to 0.1 g, and the bulk specific gravity was calculated according to the following equation.

$$\text{Bulk specific gravity [g/cm}^3\text{]}=(W2-W1)/100 \text{ cm}^3$$

(c) Water Absorption Capacity without Load (CRC)

The CRC of the water absorbent resin powder was measured in accordance with ERT441.2-02.

(d) Amount of Residual Glycidyl-Based Crosslinking Agent

The amount of the residual glycidyl-based crosslinking agent in the water absorbent resin powder was measured as follows with reference to Patent Document 12 (WO 97/03114 A) and Patent Document 13 (JP-A-7-278225).

The water absorbent resin powder in an amount of 2.0 g was added to a 100-ml beaker, and 2 ml of a composition liquid formed of methyl alcohol and water (2:1 (ratio by weight)) was added to the beaker, which was lidded and left to stand at room temperature for 1 hour. Next, 5 ml of methyl alcohol was added to the beaker, and the dispersion liquid of the water absorbent resin powder was filtered with an HPLC filter attached to a syringe to give a solution. The filtrate obtained in an amount of 1.0 g was put in a 50-ml eggplant-shaped flask, and 0.05 ml of a 12 wt % aqueous solution of nicotinamide was added. The solution was heated by a boiled water bath for 30 minutes in the eggplant-shaped flask which an air-cooled tube was attached to that the solution to be not dried and solidified, and thus the nicotinamide and the residual glycidyl-based crosslinking agent were reacted. The reaction solution was filtered with filter paper, and the filtrate was condensed, dried, and solidified. Then, an HPLC eluent was added, and the nicotinamide-glycidyl-based crosslinking agent adduct was analyzed by high performance liquid chromatography (HPLC) with UV absorption. On the other hand, the same operation was performed by using no water absorbent resin powder but adding a known amount of the glycidyl-based crosslinking agent, and the standard curve obtained was regarded as an external standard. Then, the content (ppm) of the glycidyl-based crosslinking agent (the amount of the residual glycidyl-based crosslinking agent) in the water absorbent resin powder was obtained in view of the dilution rate of the filtrate. A content of less than 1 ppm is regarded as being the detection limit or less, ND.

(e) Permeability Dependent Absorption Under Pressure (PDAUP)

The PDAUP (diffuse water absorption capacity under load) of the water absorbent resin powder was measured in accordance with the EDANA method (WSP243.3 (10)).

(f) Water Retainability (DW)

The DW of the water absorbent resin powder was measured as follows. Using a device that is illustrated in FIG. 1, a stainless-steel 400-mesh metal gauze 101 (mesh size: 38 μm) was fused with the bottom of a plastic supporting cylinder 100 having an inner diameter of 60 mm, 1.000 g±0.005 g of the water absorbent resin powder (swollen gel 102) was uniformly scattered onto the metal gauze under the conditions of room temperature (20 to 25° C.) and a humidity of 50% RH, and then the weight W5 (g) of the measuring device set was measured.

A glass filter 104 (manufactured by SOGO LABORATORY GLASS WORKS CO., LTD., fine pore diameter: 100 to 120 μm) having a diameter of 120 mm was put in a circular or square petri dish 103 having a bottom area of 400 cm$^2$, and a 10% by weight aqueous solution of sodium chloride 106 (23±0.5° C.) was added so that the aqueous solution was at the same level as the upper surface of the glass filter (the solution was kept slightly above the outer periphery of the glass filter due to surface tension, or about 50% of the surface of the glass filter was covered with the solution). A piece of filter paper 105 (ADVANTEC Toyo Kaisha, Ltd., item: (JIS P 3801, No. 2), thickness: 0.26 mm, retained particle diameter: 5 μm) having a diameter of 110 mm was placed on the solution to wet the entire filter paper.

The measuring device set was placed on the damp filter paper for solution absorption (the solution temperature is strictly controlled at 23±0.5° C. also during the measurement). After 2 minutes, the measuring device set was lifted and measured for its mass W6 (g). Then, the 2-min high-concentration salt water DW (g/g) was calculated from W5 and W6 according to the following equation.

2-min high-concentration salt water DW [g/g]={(W6−W5)/(weight of water absorbent resin powder)}

(Handleability)

In each of the tests, when it was difficult to handle the water absorbent resin powder, that is, when the water absorbent resin powder generated a problem of operability due to generation of powder dust or the like, the handleability was evaluated as "x", and an adhesion property and an aggregation property were not evaluated.

Evaluation Test 1 for Preparing Property of Heat Generating Element Composition for Pocket Warmer (Adhesion Property)

Into a SUS vessel having a capacity of 500 mL were charged with 7.5 g of the water absorbent resin powder and 30 g of activated carbon (manufactured by FUTAMURA CHEMICAL CO., LTD., product name: Taiko activated carbon P), and the water absorbent resin powder and the activated carbon were mixed uniformly using three-one motor with a two-stirring-blade (length 1.3 cm×width 7 cm) at 200 rpm of rotation frequency of stirring-blade revolutions for 2 minutes. Next, 82.5 g of a 10% by weight aqueous solution of sodium chloride was added at an adding rate of 41.25 g/min for 2 minutes while the mixture was mixed at rotation frequency of 400 rpm. Thereafter, the mixing was stopped, the SUS vessel was flipped vertically, the bottom of the vessel was tapped from above 10 times for 10 seconds to drop the prepared mixture contained in the vessel. Then, the adhesion amount of the prepared mixture remaining in the vessel was checked and evaluated as the adhesion property under the following criteria.

Percentage [%] of adhesion of prepared mixture=adhesion amount [g]/total weight [g] of materials used×100%

○: Percentage of adhesion: 20% or less

Δ: Percentage of adhesion: more than 20% and less than 50% x: Percentage of adhesion: 50% or more

Evaluation Test 2 for Preparing Property of Heat Generating Element Composition for Pocket Warmer (Aggregation Property)

In Test 1 for confirming ease of preparation of pocket warmer, after completion of adding the 10% by weight aqueous solution of sodium chloride (2 minutes), the mixture was further continuously mixed for 8 minutes. The prepared mixture obtained by mixing for a total of 10 minutes was checked for the mixing state, which was evaluated as the aggregation property under the following criteria.

Clumping amount [g] of prepared mixture=weight of prepared mixture not passing through sieve with mesh size of 11.2 mm ○: Clumping amount: 12 g or less (10% by weight or less of total weight of materials used)

x: Clumping amount: more than 12 g (more than 10% by weight of total weight of materials used)

Production Example 1

Into a polypropylene vessel having a capacity of 1 L were charged 361 g of acrylic acid, 1.52 g of polyethylene glycol diacrylate (molecular weight: 522.66, number of average ethylene oxide units: n=9) as an internal crosslinking agent, 22.03 g of a 0.1% by weight aqueous solution of trisodium diethylenetriaminepentaacetate as a chelating agent, 296 g of a 48.5% by weight aqueous solution of sodium hydroxide, and 327 g of ion-exchanged water, and the mixture was stirred and mixed to prepare an aqueous monomer solution (1). The liquid temperature of the aqueous monomer solution (1) was raised to about 80° C. by heat of neutralization.

The aqueous monomer solution (1) was continuously stirred, and 15.8 g of a 3.8% by weight aqueous solution of sodium persulfate was added at the time when the liquid temperature of the aqueous monomer solution (1) reached 78° C., to prepare a reaction solution (1).

The reaction solution (1) was immediately poured into a stainless-steel tray-type reaction device (bottom surface: 340×340 mm, height: 25 mm, inner surface: Teflon (registered trademark) coating) in open air under ambient conditions. Soon after that, a polymerization reaction was started. The stainless-steel tray-type reaction device was set at a surface temperature of 50° C. in advance using a hot plate (NEO HOTPLATE HI-1000/manufactured by Iuchi Seieido Co., Ltd.).

The polymerization reaction progressed causing swell and foam in all directions toward the above of the tray-type reaction device while generating water vapor. Thereafter, the swollen foam contracted to a size a little larger than the bottom surface of the reaction device. The polymer obtained in this operation was regarded a hydrogel crosslinked polymer (hereinafter, referred to as a "hydrogel") (1). The polymerization reaction (swelling and contraction) was finished in about 1 minute, but the hydrogel (1)$_{was}$ retained in the reaction device for the subsequent 3 minutes. This series of operations was performed in open air under ambient conditions.

Production Example 2

A hydrogel (2) was prepared by the same operations as the Production Example 1 except an aqueous monomer solution (2) prepared by 364 g of acrylic acid, 2.11 g of polyethylene glycol diacrylate (molecular weight: 522.66, number of average ethylene oxide units: n=9) as an internal crosslinking agent, 22.16 g of a 0.1% by weight aqueous solution of trisodium diethylenetriaminepentaacetate as a chelating agent, 296 g of a 48.5% by weight aqueous solution of sodium hydroxide, and 330 g of ion-exchanged water, and the mixture was used instead of the aqueous monomer solution (1).

Production Example 3

A hydrogel (3) was prepared by the same operations as the Production Example 1 except an aqueous monomer solution (3) prepared by 354 g of acrylic acid, 1.00 g of polyethylene glycol diacrylate (molecular weight: 522.66, number of average ethylene oxide units: n=9) as an internal crosslinking agent, 21.66 g of a 0.1% by weight aqueous solution of trisodium diethylenetriaminepentaacetate as a chelating agent, 296 g of a 48.5% by weight aqueous solution of sodium hydroxide, and 319 g of ion-exchanged water, and the mixture was used instead of the aqueous monomer solution (1).

Example 1

(Gel Grinding)

The hydrogel (1) obtained in Production Example 1 was subjected to gel grinding using a meat chopper (Model No. 32, manufactured by Kabushiki Kaisha Hiraga Seisakusho) equipped with a die having a die pore diameter of 9.5 mm, to give a particulate hydrogel (1). The gel grinding was performed by charging the hydrogel (1) at 2.4 (kg/min) and water vapor at 5.0 (kg/h) into the meat chopper while the screw-shaft's rotation frequency of the meat chopper was set at 130 rpm. The conditions for the gel grinding were appropriately changed so that the finally obtained water absorbent resin powder had a bulk specific gravity of 0.630 g/cm$^3$ or less.

(Drying)

Next, the particulate hydrogel (1) obtained by the gel grinding was dried using a hot air dryer to give a dried polymer (1). The drying was performed by spreading the particulate hydrogel (1) on a stainless-steel metal gauze with a mesh size of 850 µm and aerating the particulate hydrogel (1) with 180° C. hot air for 30 minutes.

(Grinding and Classifying)

Subsequently, the dried polymer (1) obtained by the drying was ground using a roll mill (WML-type roll grinder/manufactured by Yugen Kaisha Inoguchi Giken) and then classified using JIS standard sieves with mesh sizes of 850 µm and 150 µm, to give irregularly broken water absorbent resin particles (1).

(Surface Crosslinking)

Next, a (covalent bonding) surface crosslinking agent solution containing 0.375 parts by weight of ethylene carbonate, 0.63 parts by weight of propylene glycol, and 2.53 parts by weight of ion-exchanged water, relative to 100 parts by weight of the water absorbent resin particles (1) was uniformly mixed with the water absorbent resin particles (1) and heat-treated at a temperature of 198° C. for 30 minutes. Thereafter, cooling was performed, and an (ion bonding) surface crosslinking agent solution containing 0.503 parts by weight of a 27.5% by weight aqueous solution of aluminum sulfate (8% by weight in terms of aluminum oxide), 0.084 parts by weight of a 60% by weight aqueous solution of sodium lactate, and 0.012 parts by weight of propylene glycol was uniformly mixed with the water absorbent resin particles (1).

(Particle Size Regulation)

Thereafter, the particles were crushed (particle size regulation step) until the particles passed through a JIS standard sieve with a mesh size of 850 µm, to give a water absorbent resin powder (1) 99% or more of which had a particle diameter of 850 to 150 µm and which had a weight-average particle diameter (D50) of 390 µm and a bulk specific gravity of 0.590 g/cm$^3$. Table 1 shows the physical properties of the water absorbent resin powder (1).

Example 2

The hydrogel (2) obtained in Production Example 2 was subjected to gel grinding using a meat chopper (Model No. 32, manufactured by Kabushiki Kaisha Hiraga Seisakusho) equipped with a die having a die pore diameter of 9.5 mm, to give a particulate hydrogel (2). The gel grinding was performed by charging the hydrogel (2) at 2.4 (kg/min) and water vapor at 5.0 (kg/h) into the meat chopper while the number of screw-shaft's rotation frequency of the meat chopper was set at 130 rpm. The conditions for the gel grinding were appropriately changed so that the finally obtained water absorbent resin powder had a bulk specific gravity of 0.630 g/cm$^3$ or less.

(Drying)

Next, the particulate hydrogel (2) obtained by the gel grinding was dried using a hot air dryer to give a dried polymer (2). The drying was performed by spreading the particulate hydrogel (2) on a stainless-steel metal gauze with a mesh size of 850 µm and aerating the particulate hydrogel (2) with 180° C. hot air for 30 minutes.

(Grinding and Classifying)

Subsequently, the dried polymer (2) obtained by the drying was ground using a roll mill (WML-type roll grinder/manufactured by Yugen Kaisha Inoguchi Giken) and then classified using JIS standard sieves with mesh sizes of 850 µm and 150 µm, to give irregularly broken water absorbent resin particles (2).

(Surface Crosslinking)

Next, a (covalent bonding) surface crosslinking agent solution containing 0.373 parts by weight of ethylene carbonate, 0.74 parts by weight of propylene glycol, and 2.52 parts by weight of ion-exchanged water, relative to 100 parts by weight of the water absorbent resin particles (2) was uniformly mixed and heat-treated at a temperature of 198° C. for 30 minutes.

(Particle Size Regulation)

Thereafter, cooling was performed, the particles were crushed (particle size regulation step) until the particles passed through a JIS standard sieve with a mesh size of 850 µm, to give a water absorbent resin powder (2) 99% or more of which had a particle diameter of 850 to 150 µm and which had a weight-average particle diameter (D50) of 392 µm and a bulk specific gravity of 0.610 g/cm$^3$. Table 1 shows the physical properties of the water absorbent resin powder (2).

Example 3

(Resurface Crosslinking)

An (ion bonding) surface crosslinking agent solution containing 1.17 parts by weight of a 27.5% by weight aqueous solution of aluminum sulfate (8% by weight in terms of aluminum oxide), 0.196 parts by weight of a 60% by weight aqueous solution of sodium lactate, and 0.029 parts by weight of propylene glycol, relative to 100 parts by weight of the water absorbent resin powder (2) was uniformly mixed with the water absorbent resin powder (2).

(Particle Size Regulation)

Thereafter, the particles were crushed (particle size regulation step) until the particles passed through a JIS standard sieve with a mesh size of 850 µm, to give a water absorbent resin powder (3) 99% or more of which had a particle diameter of 850 to 150 µm and which had a weight-average particle diameter (D50) of 390 µm and a bulk specific gravity of 0.570 g/cm$^3$. Table 1 shows the physical properties of the water absorbent resin powder (3).

[Production Example 4] a First Type of Foaming Polymerization of Water Absorbent Resin Hydrogel (Foaming by Introducing Bubbles Derived from Dissolved Oxygen)

300.1 [g/min] of acrylic acid, 595.4 [g/min] of 37% by weight of sodium acrylate aqueous solution, 2.71 [g/min] of polyethylene glycol diacrylate (molecular weight: 522.66, number of average ethylene oxide units: n=9) as an internal cross-linking agent, 0.42 [g/min] of 31% by weight of aqueous solution of trisodium diethylenetriaminepentaacetate as a chelating agent, 198.6 [g/min] of 48% by weight of sodium hydroxide aqueous solution, 203.9 [g/min] of ion-exchanged water and 0.46 [g/min] of 10% by weight of polyoxyethylene (20) sorbitan monostearate aqueous solution as a surfactant were continuously mixed by a disperser. After passing through the disperser, the aqueous monomer solution (4) was added with 26.0 [g/min] of 3% by weight of sodium persulfate aqueous solution in the line-mixing, thereafter supplied to the belt polymerization machine. The belt polymerization machine was equipped with an endless belt having 3.8 m in length and 60 cm in width and having coated surface with a fluororesin. The belt polymerization machine has a bottom surface of the belt and the circumference of the polymerization machine heated to about 90° C. and kept warm, and equipped with an intake pipe for collecting evaporated water in the central portion. Also, the temperature of the aqueous monomer solution supplied onto the belt was controlled to 92° C. by passing water through the disperser. The temperature of the aqueous monomer solution (4) supplied to the polymerization apparatus was 92° C., and the dissolved oxygen amount was 4.30 [ml/L]. At this time, the decrease in gas solubility got the aqueous monomer solution (4) containing the surfactant turbid by the introduction of very fine bubbles. The monomer aqueous solution (4) was continuously supplied to the belt polymerization machine, and then the polymerization reaction started immediately, and polymerization was performed in the polymerization machine for about 2 minutes, to give the belt-shaped hydrogel (4).

[Example 4] a Water Absorbent Resin Powder of the Present Invention by Surface Crosslinking after Foaming Polymerization and its Production (Gel Grinding)

The hydrogel (4) obtained in Production Example 4 was cut to 200 mm in length and then subjected to gel grinding using a meat chopper (Model No. 32, manufactured by Kabushiki Kaisha Hiraga Seisakusho) equipped with a die having a die pore diameter of 7.5 mm, to give a particulate hydrogel (4). The gel grinding was performed by charging the hydrogel (4) at 1.6 (kg/min), 90° C. hot water at 50 (g/min) and water vapor at 4.2 (kg/h) into the meat chopper while the number of screw-shaft's rotation frequency of the meat chopper was set at 412 rpm.

(Drying)

Next, the particulate hydrogel (4) obtained by the gel grinding was dried using a hot air dryer to give a dried polymer (4). The drying was performed by spreading the particulate hydrogel (4) on a stainless-steel metal gauze with a mesh size of 850 µm and aerating the particulate hydrogel (4) with 180° C. hot air for 30 minutes.

(Grinding and Classifying)

Subsequently, the dried polymer (4) obtained by the drying was ground using a roll mill (WML-type roll grinder/manufactured by Yugen Kaisha Inoguchi Giken) and then classified using JIS standard sieves with mesh sizes of 850 µm and 150 µm, to give irregularly broken water absorbent resin particles (4).

(Surface Crosslinking)

Next, a (covalent bonding) surface crosslinking agent solution containing 0.4 parts by weight of ethylene carbonate, 0.6 parts by weight of propylene glycol, 2.5 parts by weight of ion-exchanged water, and 0.001 parts by weight of polyoxyethylene (20) sorbitan monostearate, relative to 100 parts by weight of the water absorbent resin particles (4) was uniformly mixed with the water absorbent resin particles (4) and heat-treated at a temperature of 180° C. for 45 minutes. Thereafter, cooling was performed, and an (ion bonding) surface crosslinking agent solution containing 0.76 parts by weight of a 27.5% by weight aqueous solution of aluminum sulfate (8% by weight in terms of aluminum oxide), 0.23 parts by weight of a 60% by weight aqueous solution of sodium lactate, and 0.06 parts by weight of propylene glycol was uniformly mixed with the water absorbent resin particles (4).

(Particle Size Regulation)

Thereafter, the particles were crushed (particle size regulation step) until the particles passed through a JIS standard sieve with a mesh size of 850 µm, to give a water absorbent resin powder (4) 99% or more of which had a particle diameter of 850 to 150 µm and which had a weight-average particle diameter (D50) of 380 µm and a bulk specific gravity of 0.610 g/cm³. Table 1 shows the physical properties of the water absorbent resin powder (4).

[Production Example 5] Another Type of Foaming Polymerization of Water Absorbent Resin Hydrogel (Foaming by Introducing Nitrogen Bubbles)

Into a beaker having a capacity of 5 L were charged 306 g of acrylic acid, 3240 g of 37 weight % sodium acrylate aqueous solution, 8.2 g of polyethylene glycol diacrylate (molecular weight: 487, number of average ethylene oxide units: n=8) as an internal crosslinking agent, 3 g of hydroxyethyl cellulose and 1420 g of ion exchanged water, and the mixture was stirred and mixed to prepare an aqueous monomer solution (5). Next, after adding 3 g of polyoxyethylene (20) sorbitan monostearate, nitrogen was blown into the monomer aqueous solution (5) to remove dissolved oxygen in the solution, and vigorously stirring with a homodisper at a high speed of 6000 rpm under a nitrogen stream to disperse a large amount of nitrogen bubbles in the monomer aqueous solution (5). When nitrogen gas was uniformly dispersed in the monomer aqueous solution (5) and its volume became 1.38 times, the monomer aqueous solution (5) with dispersed bubbles was poured into a 10 L double-arm kneader. While stirring, 10 g of a 10% by weight sodium persulfate aqueous solution and 10 g of a 10% by weight sodium bisulfite aqueous solution were added to immediately start the polymerization. Subsequently, static polymerization was performed at a temperature of 25° C. to 75° C. for 1 hour with dispersed bubbles. After the polymerization, a sponge-like hydrogel containing a large amount of bubbles was crushed into 10 mm square to 50 mm square in size by a kneader to obtain a particulate hydrogel (5).

[Example 5] a Water Absorbent Resin Powder of the Present Invention by Surface Crosslinking after Foaming Polymerization and its Production (Drying)
Next, the particulate hydrogel (5) obtained by the gel grinding was dried using a hot air dryer to give a dried polymer (5). The drying was performed by spreading the particulate hydrogel (5) on a stainless-steel metal gauze with a mesh size of 850 μm and aerating the particulate hydrogel (5) with 160° C. hot air for 60 minutes.

(Grinding and Classifying)
Subsequently, the dried polymer (5) obtained by the drying was ground using a roll mill (WML-type roll grinder/manufactured by Yugen Kaisha Inoguchi Giken) and then classified using JIS standard sieves with mesh sizes of 850 μm, to give irregularly broken water absorbent resin particles (5).

(Surface Crosslinking)
Next, a (covalent bonding) surface crosslinking agent solution containing 0.4 parts by weight of ethylene carbonate, 0.5 parts by weight of propylene glycol, and 2.5 parts by weight of ion-exchanged water, relative to 100 parts by weight of the water absorbent resin particles (5) was uniformly mixed with water absorbent resin particles (5) and heat-treated at a temperature of 197° C. for 35 minutes.

(Particle Size Regulation)
Thereafter, cooling was performed, the particles were crushed (particle size regulation step) until the particles passed through a JIS standard sieve with a mesh size of 850 μm, to give a water absorbent resin powder (5) 99% or more of which had a particle diameter of 850 to 150 μm and which had a weight-average particle diameter (D50) of 410 μm and a bulk specific gravity of 0.600 g/cm³. Table 1 shows the physical properties of the water absorbent resin powder (5).

Production Example 6

Into a polypropylene vessel having a capacity of 10 L were charged 425 g of acrylic acid, 4500 g of 37 weight % sodium acrylate aqueous solution, 4.4 g of polyethylene glycol diacrylate (molecular weight: 552.66, number of average ethylene oxide units: n=9) as an internal crosslinking agent, and the mixture was stirred and mixed to prepare an aqueous monomer solution (6). Next, nitrogen was blown into the monomer aqueous solution (6) to remove dissolved oxygen in the solution. The monomer aqueous solution (6) was poured into a 10 L double-arm kneader. While stirring, 2.8 g of sodium persulfate and 0.12 g of L-ascorbic acid were added and then the polymerization was began after 1 min of the addition. Subsequently, static polymerization was performed at a temperature of 30° C. to 90° C. for 1 hour. After the polymerization, a hydrogel was crushed into about 5 mm square in size by a kneader to obtain a particulate hydrogel (6).

[Example 6] a Water Absorbent Resin Powder of the Present Invention by Granulation and its Production (Drying)
Next, the particulate hydrogel (6) obtained by the gel grinding was dried using a hot air dryer to give a dried polymer (6). The drying was performed by spreading the particulate hydrogel (6) on a stainless-steel metal gauze with a mesh size of 300 μm and aerating the particulate hydrogel (6) with 160° C. hot air for 60 minutes.

(Grinding and Classifying)
Subsequently, the dried polymer (6) obtained by the drying was ground using a hammer mill and then classified using JIS standard sieves with mesh sizes of 180 μm, to give water absorbent resin particles (6) being fractioned by passing through a 180 μm sieve.

(Granulation)
Next, 300 g of the water-absorbent resin particles (6) was placed in 5 L of a mortar mixer manufactured by Nishi Nihon Shikenki Co., Ltd. (5 L of a container was kept warm in a bath at 80° C.), and while the stirring blade of the mortar mixer was rotated at high speed of 60 Hz/100V, 300 g of ion-exchanged water heated at 90° C. was added at once as a granulating binder for the water-absorbent resin particles (6). The water-absorbent resin particles (6) and ion-exchanged water were mixed within 10 seconds, and the entire contents became a hydrogel-like granulated product having a particle size of about 3 mm to 10 mm. After stirring at high speed in a mortar mixer for 1 minute, the drying was performed by spreading the hydrogel-like granulated product in a separate state on a stainless-steel metal gauze with a mesh size of 300 μm and aerating the product with 150° C. hot air for 60 minutes. Subsequently, the dried granulated product obtained by the drying was ground using a roll mill (WML-type roll grinder/manufactured by Yugen Kaisha Inoguchi Giken) and then classified using JIS standard sieves with mesh sizes of 850 μm and 150 μm, to give water absorbent resin granulated particles (6).

(Surface Crosslinking)
Next, a (covalent bonding) surface crosslinking agent solution containing 0.3 parts by weight of ethylene carbonate, 0.025 parts by weight of ethylene glycol diglycidyl ether, 0.5 parts by weight of propylene glycol, and 2.0 parts by weight of ion-exchanged water, relative to 100 parts by weight of the water absorbent resin granulated particles (6) was uniformly mixed with the water absorbent resin granulated particles (6) and heat-treated at a temperature of 200° C. for 50 minutes.

(Particle Size Regulation)

Thereafter, cooling was performed, the particles were crushed (particle size regulation step) until the particles passed through a JIS standard sieve with a mesh size of 850 µm, to give a water absorbent resin powder (6) 99% or more of which had a particle diameter of 850 to 150 µm and which had a weight-average particle diameter (D50) of 340 µm and a bulk specific gravity of 0.580 g/cm$^3$. Table 1 shows the physical properties of the water absorbent resin powder (6).

Comparative Example 2

(Reparticle Size Regulation)

The water absorbent resin powder (1) obtained by Example 1 were crushed (particle size regulation step) until the particles passed through a JIS standard sieve with a mesh size of 500 µm, to give a comparative water absorbent resin powder (1) 74% of which had a particle diameter of 500 to 150 µm and which had a weight-average particle diameter (D50) of 200 µm and a bulk specific gravity of 0.666 g/cm$^3$. Table 1 shows the physical properties of the comparative water absorbent resin powder (1).

Comparative Example 2

(Gel Grinding)

The hydrogel (1) obtained in Production Example 1 was subjected to gel grinding using a meat chopper (Model No. 32, manufactured by Kabushiki Kaisha Hiraga Seisakusho) equipped with a die having a die pore diameter of 11 mm, to give a comparative particulate hydrogel (2). The gel grinding was performed by charging the hydrogel (2) at 2.4 (kg/min) and water vapor at 5.0 (kg/h) into the meat chopper while the number of screw-shaft's rotation frequency of the meat chopper was set at 130 rpm.

Thereafter, the same operation as in Example (1) was performed except that the comparative particulate hydrogel (2) was used instead of the particulate hydrogel (1) of Example (1), to give a comparative water absorbent resin powder (2) 99% or more of which had a particle diameter of 850 to 150 µm and which had a weight-average particle diameter (D50) of 420 µm and a bulk specific gravity of 0.650 g/cm$^3$. Table 1 shows the physical properties of the comparative water absorbent resin powder (2).

[Comparative Example 3] (Equivalent to Patent Document 10)

A water absorbent resin powder was produced according to Example 4 of the specification of Patent Document 10 (WO 2011/126079 A). Specifically, A continuous production device was prepared being composed of a polymerization step, a gel grinding step, a drying step, a grinding step, a classifying step, a surface crosslinking step, a cooling step, a particle size regulation step, and a transportation step for connecting the steps as the water absorbent resin powder manufacturing apparatus. The production capacity of the continuous production apparatus is about 3500 [kg/hr]. The above steps may be one series or two or more series, respectively. The production capacity is shown as the total amount of each series when two or more series were used. The continuous production apparatus continuously produced water absorbent resin powder.

A comparative aqueous monomer solution (3) was prepared and composed of 193.3 parts by weight of acrylic acid, 1.26 parts by weight of polyethylene glycol diacrylate (molecular weight: 522.66, number of average ethylene oxide units: n=9) as an internal crosslinking agent, 52 parts by weight of a 0.1% by weight aqueous solution of ethylenediaminetetra (methylenephosphonic acid) 5 sodium aqueous solution as a chelating agent, 64.4 parts by weight of a 48% by weight aqueous solution of sodium hydroxide, and 134 parts by weight of ion-exchanged water.

Thereafter, the comparative aqueous monomer solution (3) with adjusted temperature of 40° C. was continuously supplied by a metering pump, and then 97.1 parts by weight of a 48% by weight sodium hydroxide aqueous solution was continuously line-mixed. The temperature of the comparative aqueous monomer solution (3) was raised to 85° C. by the neutralization heat during the mixing. Furthermore, after continuously line-mixing 8.05 parts by weight of a 4% by weight sodium persulfate aqueous solution, it is continuously supplied to a continuous polymerization machine having a planar polymerization belt with weirs at both ends so as to the thickness becomes about 7.5 mm. Thereafter, polymerization (polymerization time of 3 minutes) was continuously performed to obtain a strip-shaped comparative hydrogel (3).

(Gel Grinding)

The comparative hydrogel (3) was continuously cut at equal intervals in the width direction with respect to the traveling direction of the polymerization belt to obtain about 300 mm cutting length. The comparative hydrogel (3) was subjected to gel grinding using a meat chopper with a screw shaft diameter of 152 mm equipped with a die having a die diameter of 340 mm and a pore diameter of 22 mm, to give a comparative particulate hydrogel (3). The gel grinding was performed by charging the comparative hydrogel (3) at 132.8 (kg/min), hot water at 70° C. at 855.8 (kg/min) and water vapor at 199.8 (kg/h) into the meat chopper while the number of screw-shaft's rotation frequency of the meat chopper was set at 96 rpm.

(Drying)

Next, the comparative particulate hydrogel (3) obtained by the gel grinding was spreading on the ventilation belt within 1 minute after the gel grinding and dried at 185° C. for 30 minutes using a hot air dryer to give a comparative dried polymer (3).

(Grinding and Classifying)

Subsequently, the comparative dried polymer (3) obtained by the drying was ground using a roll mill (WML-type roll grinder/manufactured by Yugen Kaisha Inoguchi Giken) and then classified using JIS standard sieves with mesh sizes of 710 µm and 175 µm, to give irregularly broken comparative water absorbent resin particles (3).

(Surface Crosslinking)

Next, a (covalent bonding) surface crosslinking agent solution containing 0.3 parts by weight of 1,4-butanediol, 0.6 parts by weight of propylene glycol, and 3.0 parts by weight of ion-exchanged water, relative to 100 parts by weight of the comparative water absorbent resin particles (3) was uniformly mixed with the comparative water absorbent resin particles (3) and heat-treated at a temperature of 208° C. for 40 minutes. Thereafter, cooling was performed, and an (ion bonding) surface crosslinking agent solution containing 1.17 parts by weight of a 27.5% by weight aqueous solution of aluminum sulfate (8% by weight in terms of aluminum oxide), 0.196 parts by weight of a 60% by weight aqueous solution of sodium lactate, and 0.029 parts by weight of propylene glycol was uniformly mixed with the comparative water absorbent resin particles (3).

(Particle Size Regulation)

Thereafter, the particles were crushed (particle size regulation step) until the particles passed through a JIS standard sieve with a mesh size of 850 µm, to give a comparative water absorbent resin powder (3) 99% or which had a particle diameter of 850 to 150 µm and which had a weight-average particle diameter (D50) of 350 µm and a bulk specific gravity of 0.660 g/cm$^3$. Table 1 shows the physical properties of the comparative water absorbent resin powder (3).

Comparative Example 4

(Gel Grinding)

The hydrogel (3) obtained in Production Example 3 was subjected to gel grinding using a meat chopper (Model No. 32, manufactured by Kabushiki Kaisha Hiraga Seisakusho) equipped with a die having a die pore diameter of 9.5 mm, to give a comparative particulate hydrogel (4). The gel grinding was performed by charging the hydrogel (3) at 2.4 (kg/min) and water vapor at 5.0 (kg/h) into the meat chopper while the number of screw-shaft's rotation frequency of the meat chopper was set at 130 rpm. The conditions for the gel grinding were appropriately changed so that the finally obtained water absorbent resin powder had a bulk specific gravity of 0.630 g/cm$^3$ or less.

(Drying)

Next, the comparative particulate hydrogel (4) obtained by the gel grinding was dried using a hot air dryer to give a comparative dried polymer (4). The drying was performed by spreading the comparative particulate hydrogel (4) on a stainless-steel metal gauze with a mesh size of 850 µm and aerating the comparative particulate hydrogel (4) with 180° C. hot air for 30 minutes.

(Grinding and Classifying)

Subsequently, the comparative dried polymer (4) obtained by the drying was ground using a roll mill (WML-type roll grinder/manufactured by Yugen Kaisha Inoguchi Giken) and then classified using JIS standard sieves with mesh sizes of 850 µm and 150 µm, to give irregularly broken comparative water absorbent resin particles (4).

(Surface Crosslinking)

Next, a (covalent bonding) surface crosslinking agent solution containing 0.024 parts by weight of ethylene glycol diglycidyl ether (Denacol EX-810), 0.308 parts by weight of ethylene carbonate, 0.515 parts by weight of propylene glycol, and 2.08 parts by weight of ion-exchanged water, relative to 100 parts by weight of the comparative water absorbent resin particles (4) was uniformly mixed with the comparative water absorbent resin particles (4) and heat-treated at a temperature of 190° C. for 30 minutes.

Thereafter, cooling was performed, and a solution containing 0.022 parts by weight of a 45% by weight diethylenetriamine pentaacetic acid trisodium salt (CHIREST PC-45) and 1 parts by weight of ion-exchanged water was uniformly mixed with the comparative water absorbent resin particles (4).

(Particle Size Regulation)

Thereafter, the particles were crushed (particle size regulation step) until the particles passed through a JIS standard sieve with a mesh size of 850 µm, and mixed with 0.35 parts by weight of hydrophilic silica (Reorosil QS-20). The mixing was performed by shaking for 3 minutes using a mayonnaise bottle having a capacity of 225 mL, to give a comparative water absorbent resin powder (4) 99% or more of which had a particle diameter of 850 to 150 µm and which had a weight-average particle diameter (D50) of 350 µm and a bulk specific gravity of 0.610 g/cm$^3$. Table 1 shows the physical properties of the comparative water absorbent resin powder (4).

[Comparative Example 5] (Equivalent to Patent Document 15)

A water absorbent resin powder was produced according to Example 1 of Patent Document 15 (U.S. Pat. No. 5,264,850). Patent Document 15 disclosed parameters such as swelling volume; apparent density (0.55 to 0.64 g/ml); water retention amount (28 to 38 g/g in Table 3); weight average particle diameter (380 to 405 µm in Table 3). And the surface crosslinking of Patent Document 15 is similar to that of Patent Document 5, and Patent Document 5 and Patent Document 15 do not disclose the residual glycidyl crosslinking agent. That is, based on Example 1 of Patent Document 15, 108.5 parts (1.51 mol part) of acrylic acid, 0.35 part (0.0014 mol part) of pentaerythritol triallyl ether as an internal crosslinking agent, and 389.9 parts of ion-exchanged water was stirred and mixed while maintaining the temperature at 3° C. to prepare a comparative monomer aqueous solution (5). Next, nitrogen was blown into the comparative monomer aqueous solution (5) to remove dissolved oxygen in the solution and then 0.43 parts of a 1% by weight of hydrogen peroxide aqueous solution and a 0.81 parts of 2% by weight of L-ascorbic acid aqueous solution were added to initiate the polymerization. Subsequently, polymerization was performed after the temperature reached 60° C. for about 8 hours at 60° C.±2° C. to obtain a comparative particulate hydrogel (5).

(Gel Grinding)

While grinding 400 parts of the comparative hydrogel (5) obtained by above production using a meat chopper (MEAT-CHOPPER TYPE 12VR-400KSOX/made by Iizuka Industry Co., Ltd.) equipped with a die having a die pore diameter of 6.4 mm, 99.2 parts of 35% by weight of sodium hydroxide aqueous solution was added to mix and neutralize, and then 39.7 parts of polylactic acid (polylactic acid emulsion obtained by high pressure emulsification using an activator (weight average molecular weight 50,000, volume average particle diameter of 1.0 µm and an effective content of 40%) were added and mixed to give a comparative particulate hydrogel (5).

(Drying)

Next, the comparative particulate hydrogel (5) obtained by the gel grinding was dried using a hot air dryer to give a comparative dried polymer (5). The drying was performed by spreading the comparative particulate hydrogel (5) on a stainless-steel metal gauze with a mesh size of 850 µm and aerating the comparative particulate hydrogel (5) with 90° C. hot air for 30 minutes.

(Grinding and Classifying)

Subsequently, the comparative dried polymer (5) obtained by the drying was ground using a roll mill (WML-type roll grinder/manufactured by Yugen Kaisha Inoguchi Giken) and then classified using JIS standard sieves with mesh sizes of 850 µm and 150 µm, to give irregularly broken comparative water absorbent resin particles (5).

(Surface Crosslinking)

Next, 5.5 parts of a (covalent bonding) surface crosslinking agent solution consisting of a water/methanol mixed solution (water/methanol=70/30; weight ratio) containing ethylene glycol diglycidyl ether at a concentration of 9% relative to 100 parts by weight of the comparative water absorbent resin particles (5) was uniformly mixed with the comparative water absorbent resin particles (5) and heat-treated at a temperature of 198° C. for 30 minutes to give comparative water absorbent resin powder (5) 98% of which had a particle diameter of 850 to 150 µm and which had a weight-average particle diameter (D50) of 363 µm and a bulk specific gravity of 0.520 g/cm$^3$. Table 1 shows the physical properties of the comparative water absorbent resin powder (5).

TABLE 1

|  |  | D50 [μm] | bulk specific gravity [g/cm³] | CRC [g/g] | amount of a residual glycidyl-based crosslinking agent [ppm] | PDAUP [g/g] | DW [g/g] |
|---|---|---|---|---|---|---|---|
| Example 1 | water absorbent resin powder (1) | 390 | 0.590 | 31.2 | N.D. | 19.1 | 9.4 |
| Example 2 | water absorbent resin powder (2) | 392 | 0.610 | 27.2 | N.D. | 21.1 | 10.0 |
| Example 3 | water absorbent resin powder (3) | 390 | 0.570 | 27.0 | N.D. | 21.0 | 8.7 |
| Example 4 | water absorbent resin powder (4) | 380 | 0.610 | 26.8 | N.D. | 21.0 | 9.0 |
| Example 5 | water absorbent resin powder (5) | 410 | 0.600 | 30.5 | N.D. | 16.0 | 10.0 |
| Example 6 | water absorbent resin powder (6) | 345 | 0.580 | 31.8 | N.D. | 6.5 | 9.8 |
| Comparative Example 1 | comparative water absorbent resin powder (1) | 200 | 0.666 | 26.3 | N.D. | 17.2 | 12.3 |
| Comparative Example 2 | comparative water absorbent resin powder (2) | 420 | 0.650 | 29.3 | N.D. | 18.0 | 6.0 |
| Comparative Example 3 | comparative water absorbent resin powder (3) | 350 | 0.660 | 26.8 | N.D. | 18.5 | 5.8 |
| Comparative Example 4 | comparative water absorbent resin powder (4) | 350 | 0.610 | 33.0 | N.D. | 5.7 | 8.4 |
| Comparative Example 5 | comparative water absorbent resin powder (5) | 363 | 0.520 | 30.0 | 12 | 5.6 | 11.5 |

TABLE 2

|  |  |  | adhesion property | | aggregation property | |
|---|---|---|---|---|---|---|
|  |  | Handleability | Percentage [%] of adhesion of prepared mixture | evaluation | Clumping amount [g] | evaluation |
| Example 1 | water absorbent resin powder (1) | good | 10.9 | ○ | 6.2 | ○ |
| Example 2 | water absorbent resin powder (2) | good | 2.6 | ○ | 2.1 | ○ |
| Example 3 | water absorbent resin powder (3) | good | 11.0 | ○ | 7.7 | ○ |
| Example 4 | water absorbent resin powder (4) | good | 13.0 | ○ | 2.5 | ○ |
| Example 5 | water absorbent resin powder (5) | good | 7.4 | ○ | 8.3 | ○ |
| Example 6 | water absorbent resin powder (6) | good | 6.8 | ○ | 11.2 | ○ |
| Comparative Example 1 | comparative water absorbent resin powder (1) | poor | not conducted | | not conducted | |
| Comparative Example 2 | comparative water absorbent resin powder (2) | good | 51.0 | x | not conducted | |
| Comparative Example 3 | comparative water absorbent resin powder (3) | good | 52.1 | x | not conducted | |
| Comparative Example 4 | comparative water absorbent resin powder (4) | good | 9.8 | ○ | 97.5 | x |
| Comparative Example 5 | comparative water absorbent resin powder (5) | good | 3.5 | ○ | 18.2 | x |

(Result)

As shown by Examples 1 to 6 in Tables 1 and 2, the water absorbent resin powder of the present invention has good handleability. Further, when the water absorbent resin powder of the present invention is mixed with the material for a pocket warmer, the adhesion amount of the prepared mixture to the vessel was small, and the mixing can be performed without aggregation, so that good pocket warmer can be prepared.

On the other hand, as shown by Comparative Example 1, the water absorbent resin powder having a weight-average particle diameter (D50) of 200 μm has bad handleability and is unsuitable as the material for a pocket warmer.

Further, as shown by Comparative Examples 2 and 3 (corresponding to Patent Document 10), the mixing of the water absorbent resin powder having a bulk specific gravity of more than 0.630 g/cm³ with the material for a pocket warmer increases the adhesion amount of the prepared mixture to the vessel to cause trouble taking the prepared mixture out of the vessel.

As shown by Comparative Example 4, the mixing of the water absorbent resin powder having a CRC of more than 32.0 g/g and a low PDAUP with the material for a pocket warmer increases generation of aggregates (clumping) to deteriorate mixability.

As shown in Comparative Example 5 (corresponding to Example 1 in Patent Document 15), the mixing of the water absorbent resin powder even having a CRC of 32.0 g/g or less but having a low PDAUP with the material for a pocket warmer increases generation of aggregates (clumping) to deteriorate mixability.

As shown in Comparative Example 5 (corresponding to Example 1 in Patent Document 15), even if the weight-average particle diameter, the bulk specific gravity, and the CRC are adjusted in the prescribed range, the water absorbent resin powder in which a large amount of the glycidyl-based compound used as the crosslinking agent remains is not desirable in view of a safety, because the water absorbent resin powder for a pocket warmer is sometimes in indirect contact with skin. The surface crosslinking in Patent Document 15 is similar to the surface crosslinking in Patent Document 5, and Patent Documents 5 and 15 don't disclose residual glycidyl crosslinking agent. Further, Patent Document 15 discloses parameters such as swelling volume, apparent density (0.55 to 0.64 g/ml in Table 3), a water retention amount (28 to 38 g/g in Table 3), and a weight-average particle diameter (380 to 405 μm in Table 3), but does not apply the water absorbent resin powder of the present invention to a heat-generating element.

DESCRIPTION OF REFERENCE SIGNS

100 Supporting cylinder
101 Metal gauze
102 Swollen gel
103 Petri dish
104 Glass filter
105 Filter paper
106 0.9% by weight aqueous solution of sodium chloride

The invention claimed is:

1. A water absorbent resin powder for a heat-generating element composition comprising a polyacrylic acid (salt)-based water absorbent resin powder, wherein the polyacrylic acid (salt)-based water absorbent resin powder has
   a bulk specific gravity (specified by JIS K3362) of 0.630 g/cm$^3$ or less;
   fluid retention capacity without load (CRC) for a 0.9% by weight aqueous solution of sodium chloride (specified by ERT441.01-2) of 32.0 g/g or less;
   a weight-average particle diameter (specified by sieve classification) of 250 μm or more;
   an amount of a residual glycidyl-based crosslinking agent of 10 ppm or less; and
   a percentage of adhesion of 20% or less, wherein the percentage of adhesion is measured by the adhesion amount [g]/total weight [g] of materials used×100% according to Evaluation Test 1.

2. The water absorbent resin powder for a heat-generating element composition according to claim 1, wherein the polyacrylic acid (salt)-based water absorbent resin powder further has:
   permeability dependent absorption under pressure (PDAUP) (specified by WSP 243.3 (10)) of 6.0 g/g or more.

3. The water absorbent resin powder for a heat-generating element composition according to claim 1, wherein the polyacrylic acid (salt)-based water absorbent resin powder further has
   2-min water retainability DW against 10% by weight aqueous solution of sodium chloride of 8.0 g/g or more.

4. The water absorbent resin powder for a heat-generating element composition according to claim 1, wherein
   the heat-generating element composition contains activated carbon, the water absorbent resin powder and an aqueous alkali metal salt solution.

5. A heat-generating element composition comprising:
   the water absorbent resin powder according to claim 1;
   activated carbon; and
   an aqueous alkali metal salt solution.

6. The water absorbent resin powder for a heat-generating element composition according to claim 1, wherein the heat-generating element composition is a chemical pocket warmer.

7. The water absorbent resin powder for a heat-generating element composition according to claim 4, wherein the heat-generating element composition is a chemical pocket warmer.

8. The heat-generating element composition according to claim 5, wherein the heat-generating element composition is a chemical pocket warmer.

* * * * *